US009694067B2

(12) United States Patent
He et al.

(10) Patent No.: US 9,694,067 B2
(45) Date of Patent: Jul. 4, 2017

(54) MONOVALENT H5 VACCINE

(71) Applicant: TEMASEK LIFE SCIENCES LABORATORY LIMITED, Singapore (SG)

(72) Inventors: Fang He, Singapore (SG); Hwei-Sing Jimmy Kwang, Singapore (SG); Prabakaran Mookkan, Singapore (SG)

(73) Assignee: TEMASEK LIFE SCIENCES LABORATORY LIMITED, Singapore (SG)

( * ) Notice: Subject to any disclaimer, the term of this patent is extended or adjusted under 35 U.S.C. 154(b) by 0 days.

(21) Appl. No.: 15/107,074

(22) PCT Filed: Dec. 12, 2014

(86) PCT No.: PCT/SG2014/000594
§ 371 (c)(1),
(2) Date: Jun. 21, 2016

(87) PCT Pub. No.: WO2015/099609
PCT Pub. Date: Jul. 2, 2015

(65) Prior Publication Data
US 2017/0000877 A1    Jan. 5, 2017

Related U.S. Application Data

(60) Provisional application No. 61/920,187, filed on Dec. 23, 2013.

(51) Int. Cl.
| | |
|---|---|
| *A61K 39/145* | (2006.01) |
| *C12N 7/00* | (2006.01) |
| *A61K 39/12* | (2006.01) |
| *C07K 14/005* | (2006.01) |
| *A61K 39/00* | (2006.01) |

(52) U.S. Cl.
CPC ............ *A61K 39/145* (2013.01); *A61K 39/12* (2013.01); *C07K 14/005* (2013.01); *C12N 7/00* (2013.01); *A61K 2039/5252* (2013.01); *C12N 2760/16122* (2013.01); *C12N 2760/16134* (2013.01); *C12N 2760/16143* (2013.01); *C12N 2760/16171* (2013.01)

(58) Field of Classification Search
CPC ............... A61K 39/12; A61K 39/145; A61K 2039/55566; A61K 39/00; A61K 2039/53; A61K 2039/552; A61K 2039/525; A61K 39/42; A61K 2039/6075; C12N 2760/16134; C12N 7/00; C12N 2760/16151; C12N 2760/16034; C12N 2760/16122; C12N 2760/16171; C07K 16/1018; C07K 16/10
See application file for complete search history.

(56) References Cited

FOREIGN PATENT DOCUMENTS

| WO | 2008/033105 A1 | 3/2008 |
|---|---|---|
| WO | 2011/136738 A1 | 11/2011 |

OTHER PUBLICATIONS

International Search Report and Written Opinion mailed Jan. 19, 2015, International Application No. PCT/SG2014/000594, 10 pages.

*Primary Examiner* — Rachel B Gill
(74) *Attorney, Agent, or Firm* — Rothwell, Figg, Ernst & Manbeck, P.C.

(57) ABSTRACT

The present invention relates to a monovalent H5N1 vaccine. More specifically, the present invention relates to the development of a monovalent H5 vaccine strain using hemagglutinin (HA) engineering to elicit cross-clade protection. The present invention also relates to an epitope-chimeric H5 and to a reverse genetics (RG) influenza virus expressing the epitope-chimeric H5.

32 Claims, 7 Drawing Sheets

SEQUENCE LISTING

```
<160> NUMBER OF SEQ ID NOS: 11

<210> SEQ ID NO 1
<211> LENGTH: 1707
<212> TYPE: DNA
<213> ORGANISM: Avian influenza virus
<220> FEATURE:
<221> NAME/KEY: CDS
<222> LOCATION: (1)..(1704)

<400> SEQUENCE: 1 atg gag aaa ata gtg ctt ctt ctt gca ata gtc agt ctt gtt aaa agt        48
Met Glu Lys Ile Val Leu Leu Leu Ala Ile Val Ser Leu Val Lys Ser
1               5                   10                  15 gat cag att tgc att ggt tac cat gca aac aat tca aca gag cag gtt        96
Asp Gln Ile Cys Ile Gly Tyr His Ala Asn Asn Ser Thr Glu Gln Val
            20                  25                  30 gac aca atc atg gaa aag aac gtt act gtt aca cat gcc caa gac ata       144
Asp Thr Ile Met Glu Lys Asn Val Thr Val Thr His Ala Gln Asp Ile
        35                  40                  45 ctg gaa aag aca cac aac ggg aag ctc tgc gat cta gat gga gtg aag       192
Leu Glu Lys Thr His Asn Gly Lys Leu Cys Asp Leu Asp Gly Val Lys
    50                  55                  60
```

| | | |
|---|---|---|
| cct cta att tta aga gat tgt agt gta gct gga tgg ctc ctc ggg aac<br>Pro Leu Ile Leu Arg Asp Cys Ser Val Ala Gly Trp Leu Leu Gly Asn<br>65                                70                        75                    80 | 240 |
| cca atg tgt gac gaa ttc atc aat gta ccg gaa tgg tct tac ata gtg<br>Pro Met Cys Asp Glu Phe Ile Asn Val Pro Glu Trp Ser Tyr Ile Val<br>                         85                     90                       95 | 288 |
| gag aag gcc aat cca acc aat gac ctc tgt tac cca ggg agt ttc aac<br>Glu Lys Ala Asn Pro Thr Asn Asp Leu Cys Tyr Pro Gly Ser Phe Asn<br>                    100                 105                 110 | 336 |
| gac tat gaa gaa ctg aaa cat cta ttg agc aga ata aac cat ttt gag<br>Asp Tyr Glu Glu Leu Lys His Leu Leu Ser Arg Ile Asn His Phe Glu<br>        115                 120                 125 | 384 |
| aaa att caa atc atc ccc aaa agt tct tgg tcc gat cat gaa gcc tca<br>Lys Ile Gln Ile Ile Pro Lys Ser Ser Trp Ser Asp His Glu Ala Ser<br>130                              135                        140 | 432 |
| tca gga gtg agc tca gca tgt cca tac ctg gga agt ccc tcc ttt ttt<br>Ser Gly Val Ser Ser Ala Cys Pro Tyr Leu Gly Ser Pro Ser Phe Phe<br>145                              150                        155                        160 | 480 |
| aga aat gtg gta tgg ctt atc aaa aag aac agt aca tac cca aca ata<br>Arg Asn Val Val Trp Leu Ile Lys Lys Asn Ser Thr Tyr Pro Thr Ile<br>                         165                        170                     175 | 528 |
| aag aaa agc tac aat aat acc aac caa gaa gat ctt ttg gta ctg tgg<br>Lys Lys Ser Tyr Asn Asn Thr Asn Gln Glu Asp Leu Leu Val Leu Trp<br>        180                 185                 190 | 576 |
| gga att cac cat cct aat gat gcg gca gag cag aca agg cta tat caa<br>Gly Ile His His Pro Asn Asp Ala Ala Glu Gln Thr Arg Leu Tyr Gln<br>             195                 200                 205 | 624 |
| aac cca acc acc tat att tcc att ggg aca tca aca cta aac cag aga<br>Asn Pro Thr Thr Tyr Ile Ser Ile Gly Thr Ser Thr Leu Asn Gln Arg<br>210                              215                        220 | 672 |
| ttg gta cca aaa ata gct act aga tcc aaa gta aac ggg caa agt gga<br>Leu Val Pro Lys Ile Ala Thr Arg Ser Lys Val Asn Gly Gln Ser Gly<br>225                              230                        235                     240 | 720 |
| agg atg gag ttc ttc tgg gca att tta aaa cct aat gat gca atc aac<br>Arg Met Glu Phe Phe Trp Ala Ile Leu Lys Pro Asn Asp Ala Ile Asn<br>                       245                     250                   255 | 768 |
| ttc gag agt aat gga aat ttc att gct cca gaa tat gca tac aaa att<br>Phe Glu Ser Asn Gly Asn Phe Ile Ala Pro Glu Tyr Ala Tyr Lys Ile<br>        260                 265                 270 | 816 |
| gtc aag aaa ggg gac tca gca att atg aaa agt gaa ttg gaa tat ggt<br>Val Lys Lys Gly Asp Ser Ala Ile Met Lys Ser Glu Leu Glu Tyr Gly<br>             275                 280                 285 | 864 |
| aac tgc aac acc aag tgt caa act cca atg ggg gcg ata aac tct agt<br>Asn Cys Asn Thr Lys Cys Gln Thr Pro Met Gly Ala Ile Asn Ser Ser<br>290                              295                        300 | 912 |
| atg cca ttc cac aac ata cac cct ctc acc atc ggg gaa tgc ccc aaa<br>Met Pro Phe His Asn Ile His Pro Leu Thr Ile Gly Glu Cys Pro Lys<br>305                              310                        315                     320 | 960 |
| tat gtg aaa tca aac aga tta gtc ctt gca aca ggg ctc aga aat agc<br>Tyr Val Lys Ser Asn Arg Leu Val Leu Ala Thr Gly Leu Arg Asn Ser<br>                       325                     330                   335 | 1008 |
| cct caa aga gag agc aga aga aaa aag aga gga cta ttt gga gct ata<br>Pro Gln Arg Glu Ser Arg Arg Lys Lys Arg Gly Leu Phe Gly Ala Ile<br>        340                 345                 350 | 1056 |
| gca ggt ttt ata gag gga gga tgg cag gga atg gta gat ggc tgg tat<br>Ala Gly Phe Ile Glu Gly Gly Trp Gln Gly Met Val Asp Gly Trp Tyr<br>             355                 360                 365 | 1104 |
| ggg tac cac cat agc aat gag cag ggg agt ggg tac gct gca gac aaa<br>Gly Tyr His His Ser Asn Glu Gln Gly Ser Gly Tyr Ala Ala Asp Lys<br>370                              375                        380 | 1152 |

```
gaa tcc act caa aag gca ata gat gga gtc acc aat aag gtc aac tca    1200
Glu Ser Thr Gln Lys Ala Ile Asp Gly Val Thr Asn Lys Val Asn Ser
385                 390                 395                 400 att att gac aaa atg aac act cag ttt gag gct gtt gga agg gaa ttt    1248
Ile Ile Asp Lys Met Asn Thr Gln Phe Glu Ala Val Gly Arg Glu Phe
                405                 410                 415 aat aac tta gaa agg aga ata gag aat tta aac aag aag atg gaa gac    1296
Asn Asn Leu Glu Arg Arg Ile Glu Asn Leu Asn Lys Lys Met Glu Asp
            420                 425                 430 ggg ttt cta gat gtt tgg act tat aat gcc gaa ctt ctg gtt ctc atg    1344
Gly Phe Leu Asp Val Trp Thr Tyr Asn Ala Glu Leu Leu Val Leu Met
        435                 440                 445 gaa aat gag aga act cta gac ttt cat gac tca aat gtt aag aac ctc    1392
Glu Asn Glu Arg Thr Leu Asp Phe His Asp Ser Asn Val Lys Asn Leu
    450                 455                 460 tac gac aag gtc cga cta cag ctt agg gat aat gca aaa gag ctg ggt    1440
Tyr Asp Lys Val Arg Leu Gln Leu Arg Asp Asn Ala Lys Glu Leu Gly
465                 470                 475                 480 aac ggt tgt ttc gag ttc tat cac aaa tgt gat aat gaa tgt atg gaa    1488
Asn Gly Cys Phe Glu Phe Tyr His Lys Cys Asp Asn Glu Cys Met Glu
                485                 490                 495 agt ata aga aac gga acg tac aac tat ccg cag tat tca gaa gaa gca    1536
Ser Ile Arg Asn Gly Thr Tyr Asn Tyr Pro Gln Tyr Ser Glu Glu Ala
            500                 505                 510 aga tta aaa aga gag gaa ata agt ggg gta aaa ttg gaa tca ata gga    1584
Arg Leu Lys Arg Glu Glu Ile Ser Gly Val Lys Leu Glu Ser Ile Gly
        515                 520                 525 act tac caa ata ctg tca att tat tca aca gta gcg agt tcc cta gca    1632
Thr Tyr Gln Ile Leu Ser Ile Tyr Ser Thr Val Ala Ser Ser Leu Ala
    530                 535                 540 ctg gca atc atg ata gct ggt cta tct tta tgg atg tgc tcc aat gga    1680
Leu Ala Ile Met Ile Ala Gly Leu Ser Leu Trp Met Cys Ser Asn Gly
545                 550                 555                 560 tcg tta caa tgc aga att tgc att taa                                1707
Ser Leu Gln Cys Arg Ile Cys Ile
                565

<210> SEQ ID NO 2
<211> LENGTH: 568
<212> TYPE: PRT
<213> ORGANISM: Avian influenza virus

<400> SEQUENCE: 2

Met Glu Lys Ile Val Leu Leu Leu Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Asn Pro Thr Asn Asp Leu Cys Tyr Pro Gly Ser Phe Asn
            100                 105                 110

Asp Tyr Glu Glu Leu Lys His Leu Leu Ser Arg Ile Asn His Phe Glu
```

```
            115                 120                 125
Lys Ile Gln Ile Ile Pro Lys Ser Ser Trp Ser Asp His Glu Ala Ser
130                 135                 140

Ser Gly Val Ser Ser Ala Cys Pro Tyr Leu Gly Ser Pro Ser Phe Phe
145                 150                 155                 160

Arg Asn Val Val Trp Leu Ile Lys Lys Asn Ser Thr Tyr Pro Thr Ile
                    165                 170                 175

Lys Lys Ser Tyr Asn Asn Thr Asn Gln Glu Asp Leu Leu Val Leu Trp
                180                 185                 190

Gly Ile His His Pro Asn Asp Ala Ala Glu Gln Thr Arg Leu Tyr Gln
            195                 200                 205

Asn Pro Thr Thr Tyr Ile Ser Ile Gly Thr Ser Thr Leu Asn Gln Arg
        210                 215                 220

Leu Val Pro Lys Ile Ala Thr Arg Ser Lys Val Asn Gly Gln Ser Gly
225                 230                 235                 240

Arg Met Glu Phe Phe Trp Ala Ile Leu Lys Pro Asn Asp Ala Ile Asn
                    245                 250                 255

Phe Glu Ser Asn Gly Asn Phe Ile Ala Pro Glu Tyr Ala Tyr Lys Ile
                260                 265                 270

Val Lys Lys Gly Asp Ser Ala Ile Met Lys Ser Glu Leu Glu Tyr Gly
            275                 280                 285

Asn Cys Asn Thr Lys Cys Gln Thr Pro Met Gly Ala Ile Asn Ser Ser
        290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Ser
                    325                 330                 335

Pro Gln Arg Glu Ser Arg Arg Lys Lys Arg Gly Leu Phe Gly Ala Ile
                340                 345                 350

Ala Gly Phe Ile Glu Gly Gly Trp Gln Gly Met Val Asp Gly Trp Tyr
            355                 360                 365

Gly Tyr His His Ser Asn Glu Gln Gly Ser Gly Tyr Ala Ala Asp Lys
        370                 375                 380

Glu Ser Thr Gln Lys Ala Ile Asp Gly Val Thr Asn Lys Val Asn Ser
385                 390                 395                 400

Ile Ile Asp Lys Met Asn Thr Gln Phe Glu Ala Val Gly Arg Glu Phe
                    405                 410                 415

Asn Asn Leu Glu Arg Arg Ile Glu Asn Leu Asn Lys Lys Met Glu Asp
                420                 425                 430

Gly Phe Leu Asp Val Trp Thr Tyr Asn Ala Glu Leu Leu Val Leu Met
            435                 440                 445

Glu Asn Glu Arg Thr Leu Asp Phe His Asp Ser Asn Val Lys Asn Leu
        450                 455                 460

Tyr Asp Lys Val Arg Leu Gln Leu Arg Asp Asn Ala Lys Glu Leu Gly
465                 470                 475                 480

Asn Gly Cys Phe Glu Phe Tyr His Lys Cys Asp Asn Glu Cys Met Glu
                    485                 490                 495

Ser Ile Arg Asn Gly Thr Tyr Asn Tyr Pro Gln Tyr Ser Glu Glu Ala
                500                 505                 510

Arg Leu Lys Arg Glu Glu Ile Ser Gly Val Lys Leu Glu Ser Ile Gly
            515                 520                 525

Thr Tyr Gln Ile Leu Ser Ile Tyr Ser Thr Val Ala Ser Ser Leu Ala
        530                 535                 540
```

Leu Ala Ile Met Ile Ala Gly Leu Ser Leu Trp Met Cys Ser Asn Gly
545                 550                 555                 560

Ser Leu Gln Cys Arg Ile Cys Ile
                565

<210> SEQ ID NO 3
<211> LENGTH: 1656
<212> TYPE: DNA
<213> ORGANISM: Avian influenza virus
<220> FEATURE:
<221> NAME/KEY: CDS
<222> LOCATION: (1)..(1656)

<400> SEQUENCE: 3

| | |
|---|---:|
| gat cag att tgc att ggt tac cat gca aac aat tca aca gag cag gtt<br>Asp Gln Ile Cys Ile Gly Tyr His Ala Asn Asn Ser Thr Glu Gln Val<br>1               5                   10                  15 | 48 |
| gac aca atc atg gaa aag aac gtt act gtt aca cat gcc caa gac ata<br>Asp Thr Ile Met Glu Lys Asn Val Thr Val Thr His Ala Gln Asp Ile<br>            20                  25                  30 | 96 |
| ctg gaa aag aca cac aac ggg aag ctc tgc gat cta gat gga gtg aag<br>Leu Glu Lys Thr His Asn Gly Lys Leu Cys Asp Leu Asp Gly Val Lys<br>        35                  40                  45 | 144 |
| cct cta att tta aga gat tgt agt gta gct gga tgg ctc ctc ggg aac<br>Pro Leu Ile Leu Arg Asp Cys Ser Val Ala Gly Trp Leu Leu Gly Asn<br>    50                  55                  60 | 192 |
| cca atg tgt gac gaa ttc atc aat gta ccg gaa tgg tct tac ata gtg<br>Pro Met Cys Asp Glu Phe Ile Asn Val Pro Glu Trp Ser Tyr Ile Val<br>65                  70                  75                  80 | 240 |
| gag aag gcc aat cca acc aat gac ctc tgt tac cca ggg agt ttc aac<br>Glu Lys Ala Asn Pro Thr Asn Asp Leu Cys Tyr Pro Gly Ser Phe Asn<br>                85                  90                  95 | 288 |
| gac tat gaa gaa ctg aaa cat cta ttg agc aga ata aac cat ttt gag<br>Asp Tyr Glu Glu Leu Lys His Leu Leu Ser Arg Ile Asn His Phe Glu<br>            100                 105                 110 | 336 |
| aaa att caa atc atc ccc aaa agt tct tgg tcc gat cat gaa gcc tca<br>Lys Ile Gln Ile Ile Pro Lys Ser Ser Trp Ser Asp His Glu Ala Ser<br>        115                 120                 125 | 384 |
| tca gga gtg agc tca gca tgt cca tac ctg gga agt ccc tcc ttt ttt<br>Ser Gly Val Ser Ser Ala Cys Pro Tyr Leu Gly Ser Pro Ser Phe Phe<br>    130                 135                 140 | 432 |
| aga aat gtg gta tgg ctt atc aaa aag aac agt aca tac cca aca ata<br>Arg Asn Val Val Trp Leu Ile Lys Lys Asn Ser Thr Tyr Pro Thr Ile<br>145                 150                 155                 160 | 480 |
| aag aaa agc tac aat aat acc aac caa gaa gat ctt ttg gta ctg tgg<br>Lys Lys Ser Tyr Asn Asn Thr Asn Gln Glu Asp Leu Leu Val Leu Trp<br>                165                 170                 175 | 528 |
| gga att cac cat cct aat gat gcg gca gag cag aca agg cta tat caa<br>Gly Ile His His Pro Asn Asp Ala Ala Glu Gln Thr Arg Leu Tyr Gln<br>            180                 185                 190 | 576 |
| aac cca acc acc tat att tcc att ggg aca tca aca cta aac cag aga<br>Asn Pro Thr Thr Tyr Ile Ser Ile Gly Thr Ser Thr Leu Asn Gln Arg<br>        195                 200                 205 | 624 |
| ttg gta cca aaa ata gct act aga tcc aaa gta aac ggg caa agt gga<br>Leu Val Pro Lys Ile Ala Thr Arg Ser Lys Val Asn Gly Gln Ser Gly<br>    210                 215                 220 | 672 |
| agg atg gag ttc ttc tgg gca att tta aaa cct aat gat gca atc aac<br>Arg Met Glu Phe Phe Trp Ala Ile Leu Lys Pro Asn Asp Ala Ile Asn<br>225                 230                 235                 240 | 720 |
| ttc gag agt aat gga aat ttc att gct cca gaa tat gca tac aaa att<br> | 768 |

```
                Phe Glu Ser Asn Gly Asn Phe Ile Ala Pro Glu Tyr Ala Tyr Lys Ile
                                245                 250                 255 gtc aag aaa ggg gac tca gca att atg aaa agt gaa ttg gaa tat ggt          816
Val Lys Lys Gly Asp Ser Ala Ile Met Lys Ser Glu Leu Glu Tyr Gly
            260                 265                 270 aac tgc aac acc aag tgt caa act cca atg ggg gcg ata aac tct agt          864
Asn Cys Asn Thr Lys Cys Gln Thr Pro Met Gly Ala Ile Asn Ser Ser
            275                 280                 285 atg cca ttc cac aac ata cac cct ctc acc atc ggg gaa tgc ccc aaa          912
Met Pro Phe His Asn Ile His Pro Leu Thr Ile Gly Glu Cys Pro Lys
            290                 295                 300 tat gtg aaa tca aac aga tta gtc ctt gca aca ggg ctc aga aat agc          960
Tyr Val Lys Ser Asn Arg Leu Val Leu Ala Thr Gly Leu Arg Asn Ser
305                 310                 315                 320 cct caa aga gag agc aga aga aaa aag aga gga cta ttt gga gct ata         1008
Pro Gln Arg Glu Ser Arg Arg Lys Lys Arg Gly Leu Phe Gly Ala Ile
                325                 330                 335 gca ggt ttt ata gag gga gga tgg cag gga atg gta gat ggc tgg tat         1056
Ala Gly Phe Ile Glu Gly Gly Trp Gln Gly Met Val Asp Gly Trp Tyr
            340                 345                 350 ggg tac cac cat agc aat gag cag ggg agt ggg tac gct gca gac aaa         1104
Gly Tyr His His Ser Asn Glu Gln Gly Ser Gly Tyr Ala Ala Asp Lys
            355                 360                 365 gaa tcc act caa aag gca ata gat gga gtc acc aat aag gtc aac tca         1152
Glu Ser Thr Gln Lys Ala Ile Asp Gly Val Thr Asn Lys Val Asn Ser
370                 375                 380 att att gac aaa atg aac act cag ttt gag gct gtt gga agg gaa ttt         1200
Ile Ile Asp Lys Met Asn Thr Gln Phe Glu Ala Val Gly Arg Glu Phe
385                 390                 395                 400 aat aac tta gaa agg aga ata gag aat tta aac aag aag atg gaa gac         1248
Asn Asn Leu Glu Arg Arg Ile Glu Asn Leu Asn Lys Lys Met Glu Asp
                405                 410                 415 ggg ttt cta gat gtt tgg act tat aat gcc gaa ctt ctg gtt ctc atg         1296
Gly Phe Leu Asp Val Trp Thr Tyr Asn Ala Glu Leu Leu Val Leu Met
            420                 425                 430 gaa aat gag aga act cta gac ttt cat gac tca aat gtt aag aac ctc         1344
Glu Asn Glu Arg Thr Leu Asp Phe His Asp Ser Asn Val Lys Asn Leu
            435                 440                 445 tac gac aag gtc cga cta cag ctt agg gat aat gca aaa gag ctg ggt         1392
Tyr Asp Lys Val Arg Leu Gln Leu Arg Asp Asn Ala Lys Glu Leu Gly
450                 455                 460 aac ggt tgt ttc gag ttc tat cac aaa tgt gat aat gaa tgt atg gaa         1440
Asn Gly Cys Phe Glu Phe Tyr His Lys Cys Asp Asn Glu Cys Met Glu
465                 470                 475                 480 agt ata aga aac gga acg tac aac tat ccg cag tat tca gaa gaa gca         1488
Ser Ile Arg Asn Gly Thr Tyr Asn Tyr Pro Gln Tyr Ser Glu Glu Ala
                485                 490                 495 aga tta aaa aga gag gaa ata agt ggg gta aaa ttg gaa tca ata gga         1536
Arg Leu Lys Arg Glu Glu Ile Ser Gly Val Lys Leu Glu Ser Ile Gly
            500                 505                 510 act tac caa ata ctg tca att tat tca aca gta gcg agt tcc cta gca         1584
Thr Tyr Gln Ile Leu Ser Ile Tyr Ser Thr Val Ala Ser Ser Leu Ala
            515                 520                 525 ctg gca atc atg ata gct ggt cta tct tta tgg atg tgc tcc aat gga         1632
Leu Ala Ile Met Ile Ala Gly Leu Ser Leu Trp Met Cys Ser Asn Gly
            530                 535                 540 tcg tta caa tgc aga att tgc att                                         1656
Ser Leu Gln Cys Arg Ile Cys Ile
545                 550
```

<210> SEQ ID NO 4
<211> LENGTH: 552
<212> TYPE: PRT
<213> ORGANISM: Avian influenza virus

<400> SEQUENCE: 4

| Asp | Gln | Ile | Cys | Ile | Gly | Tyr | His | Ala | Asn | Asn | Ser | Thr | Glu | Gln | Val |
| 1 | | | | 5 | | | | | 10 | | | | | 15 | |

| Asp | Thr | Ile | Met | Glu | Lys | Asn | Val | Thr | Val | Thr | His | Ala | Gln | Asp | Ile |
| | | | 20 | | | | | 25 | | | | | 30 | | |

| Leu | Glu | Lys | Thr | His | Asn | Gly | Lys | Leu | Cys | Asp | Leu | Asp | Gly | Val | Lys |
| | | | 35 | | | | 40 | | | | | 45 | | | |

| Pro | Leu | Ile | Leu | Arg | Asp | Cys | Ser | Val | Ala | Gly | Trp | Leu | Leu | Gly | Asn |
| 50 | | | | | 55 | | | | | 60 | | | | | |

| Pro | Met | Cys | Asp | Glu | Phe | Ile | Asn | Val | Pro | Glu | Trp | Ser | Tyr | Ile | Val |
| 65 | | | | 70 | | | | | 75 | | | | | 80 | |

| Glu | Lys | Ala | Asn | Pro | Thr | Asn | Asp | Leu | Cys | Tyr | Pro | Gly | Ser | Phe | Asn |
| | | | | 85 | | | | | 90 | | | | | 95 | |

| Asp | Tyr | Glu | Glu | Leu | Lys | His | Leu | Leu | Ser | Arg | Ile | Asn | His | Phe | Glu |
| | | | 100 | | | | | 105 | | | | | 110 | | |

| Lys | Ile | Gln | Ile | Ile | Pro | Lys | Ser | Ser | Trp | Ser | Asp | His | Glu | Ala | Ser |
| | | | 115 | | | | | 120 | | | | | 125 | | |

| Ser | Gly | Val | Ser | Ser | Ala | Cys | Pro | Tyr | Leu | Gly | Ser | Pro | Ser | Phe | Phe |
| 130 | | | | | 135 | | | | | 140 | | | | | |

| Arg | Asn | Val | Val | Trp | Leu | Ile | Lys | Lys | Asn | Ser | Thr | Tyr | Pro | Thr | Ile |
| 145 | | | | 150 | | | | | 155 | | | | | 160 | |

| Lys | Lys | Ser | Tyr | Asn | Asn | Thr | Asn | Gln | Glu | Asp | Leu | Leu | Val | Leu | Trp |
| | | | | 165 | | | | | 170 | | | | | 175 | |

| Gly | Ile | His | His | Pro | Asn | Asp | Ala | Ala | Glu | Gln | Thr | Arg | Leu | Tyr | Gln |
| | | | 180 | | | | | 185 | | | | | 190 | | |

| Asn | Pro | Thr | Thr | Tyr | Ile | Ser | Ile | Gly | Thr | Ser | Thr | Leu | Asn | Gln | Arg |
| | | | 195 | | | | | 200 | | | | | 205 | | |

| Leu | Val | Pro | Lys | Ile | Ala | Thr | Arg | Ser | Lys | Val | Asn | Gly | Gln | Ser | Gly |
| 210 | | | | | 215 | | | | | 220 | | | | | |

| Arg | Met | Glu | Phe | Phe | Trp | Ala | Ile | Leu | Lys | Pro | Asn | Asp | Ala | Ile | Asn |
| 225 | | | | 230 | | | | | 235 | | | | | 240 | |

| Phe | Glu | Ser | Asn | Gly | Asn | Phe | Ile | Ala | Pro | Glu | Tyr | Ala | Tyr | Lys | Ile |
| | | | | 245 | | | | | 250 | | | | | 255 | |

| Val | Lys | Lys | Gly | Asp | Ser | Ala | Ile | Met | Lys | Ser | Glu | Leu | Glu | Tyr | Gly |
| | | | 260 | | | | | 265 | | | | | 270 | | |

| Asn | Cys | Asn | Thr | Lys | Cys | Gln | Thr | Pro | Met | Gly | Ala | Ile | Asn | Ser | Ser |
| | | | 275 | | | | | 280 | | | | | 285 | | |

| Met | Pro | Phe | His | Asn | Ile | His | Pro | Leu | Thr | Ile | Gly | Glu | Cys | Pro | Lys |
| | 290 | | | | | 295 | | | | | 300 | | | | |

| Tyr | Val | Lys | Ser | Asn | Arg | Leu | Val | Leu | Ala | Thr | Gly | Leu | Arg | Asn | Ser |
| 305 | | | | | 310 | | | | | 315 | | | | | 320 |

| Pro | Gln | Arg | Glu | Ser | Arg | Arg | Lys | Lys | Arg | Gly | Leu | Phe | Gly | Ala | Ile |
| | | | | 325 | | | | | 330 | | | | | 335 | |

| Ala | Gly | Phe | Ile | Glu | Gly | Gly | Trp | Gln | Gly | Met | Val | Asp | Gly | Trp | Tyr |
| | | | 340 | | | | | 345 | | | | | 350 | | |

| Gly | Tyr | His | His | Ser | Asn | Glu | Gln | Gly | Ser | Gly | Tyr | Ala | Ala | Asp | Lys |
| | | | 355 | | | | | 360 | | | | | 365 | | |

| Glu | Ser | Thr | Gln | Lys | Ala | Ile | Asp | Gly | Val | Thr | Asn | Lys | Val | Asn | Ser |
| | 370 | | | | | 375 | | | | | 380 | | | | |

```
Ile Ile Asp Lys Met Asn Thr Gln Phe Glu Ala Val Gly Arg Glu Phe
385                 390                 395                 400

Asn Asn Leu Glu Arg Arg Ile Glu Asn Leu Asn Lys Lys Met Glu Asp
            405                 410                 415

Gly Phe Leu Asp Val Trp Thr Tyr Asn Ala Glu Leu Leu Val Leu Met
        420                 425                 430

Glu Asn Glu Arg Thr Leu Asp Phe His Asp Ser Asn Val Lys Asn Leu
    435                 440                 445

Tyr Asp Lys Val Arg Leu Gln Leu Arg Asp Asn Ala Lys Glu Leu Gly
450                 455                 460

Asn Gly Cys Phe Glu Phe Tyr His Lys Cys Asp Asn Glu Cys Met Glu
465                 470                 475                 480

Ser Ile Arg Asn Gly Thr Tyr Asn Tyr Pro Gln Tyr Ser Glu Glu Ala
                485                 490                 495

Arg Leu Lys Arg Glu Glu Ile Ser Gly Val Lys Leu Glu Ser Ile Gly
            500                 505                 510

Thr Tyr Gln Ile Leu Ser Ile Tyr Ser Thr Val Ala Ser Ser Leu Ala
        515                 520                 525

Leu Ala Ile Met Ile Ala Gly Leu Ser Leu Trp Met Cys Ser Asn Gly
    530                 535                 540

Ser Leu Gln Cys Arg Ile Cys Ile
545                 550

<210> SEQ ID NO 5
<211> LENGTH: 1656
<212> TYPE: DNA
<213> ORGANISM: Avian influenza virus
<220> FEATURE:
<221> NAME/KEY: CDS
<222> LOCATION: (1)..(1656)

<400> SEQUENCE: 5 gat cag att tgc att ggt tac cat gca aac aat tca aca gag cag gtt      48
Asp Gln Ile Cys Ile Gly Tyr His Ala Asn Asn Ser Thr Glu Gln Val
1               5                   10                  15 gac aca atc atg gaa aag aac gtt act gtt aca cat gcc caa gac ata      96
Asp Thr Ile Met Glu Lys Asn Val Thr Val Thr His Ala Gln Asp Ile
            20                  25                  30 ctg gaa aag aca cac aac ggg aag ctc tgc gat cta gat gga gtg aag     144
Leu Glu Lys Thr His Asn Gly Lys Leu Cys Asp Leu Asp Gly Val Lys
        35                  40                  45 cct cta att tta aga gat tgt agt gta gct gga tgg ctc ctc ggg aac     192
Pro Leu Ile Leu Arg Asp Cys Ser Val Ala Gly Trp Leu Leu Gly Asn
    50                  55                  60 cca atg tgt gac gaa ttc atc aat gta ccg gaa tgg tct tac ata gtg     240
Pro Met Cys Asp Glu Phe Ile Asn Val Pro Glu Trp Ser Tyr Ile Val
65                  70                  75                  80 gag aag gcc aat cca acc aat gac ctc tgt tac cca ggg agt ttc aac     288
Glu Lys Ala Asn Pro Thr Asn Asp Leu Cys Tyr Pro Gly Ser Phe Asn
                85                  90                  95 gac tat gaa gaa ctg aaa cat cta ttg agc aga ata aac cat ttt gag     336
Asp Tyr Glu Glu Leu Lys His Leu Leu Ser Arg Ile Asn His Phe Glu
            100                 105                 110 aaa att caa atc atc ccc aaa agt tct tgg tcc gat cat gaa gcc tca     384
Lys Ile Gln Ile Ile Pro Lys Ser Ser Trp Ser Asp His Glu Ala Ser
        115                 120                 125 tca gga gtg agc tca gca tgt cca tac ctg gga agt ccc tcc ttt ttt     432
Ser Gly Val Ser Ser Ala Cys Pro Tyr Leu Gly Ser Pro Ser Phe Phe
```

-continued

```
            130                 135                 140
aga aat gtg gta tgg ctt atc aaa aag aac aat gca tac cca aca ata    480
Arg Asn Val Val Trp Leu Ile Lys Lys Asn Asn Ala Tyr Pro Thr Ile
145                 150                 155                 160 aag aaa agc tac aat aat acc aac caa gaa gat ctt ttg gta ctg tgg    528
Lys Lys Ser Tyr Asn Asn Thr Asn Gln Glu Asp Leu Leu Val Leu Trp
                165                 170                 175 gga att cac cat cct aat gat gcg gca gag cag aca aag cta tat caa    576
Gly Ile His His Pro Asn Asp Ala Ala Glu Gln Thr Lys Leu Tyr Gln
            180                 185                 190 aac cca acc acc tat att tcc att ggg aca tca aca cta aac cag aga    624
Asn Pro Thr Thr Tyr Ile Ser Ile Gly Thr Ser Thr Leu Asn Gln Arg
        195                 200                 205 ttg gta cca aaa ata gct act aga tcc aaa gta aac ggg caa agt gga    672
Leu Val Pro Lys Ile Ala Thr Arg Ser Lys Val Asn Gly Gln Ser Gly
    210                 215                 220 agg atg gag ttc ttc tgg gca att tta aaa cct aat gat gca atc aac    720
Arg Met Glu Phe Phe Trp Ala Ile Leu Lys Pro Asn Asp Ala Ile Asn
225                 230                 235                 240 ttc gag agt aat gga aat ttc att gct cca gaa tat gca tac aaa att    768
Phe Glu Ser Asn Gly Asn Phe Ile Ala Pro Glu Tyr Ala Tyr Lys Ile
                245                 250                 255 gtc aag aaa ggg gac tca gca att atg aaa agt gaa ttg gaa tat ggt    816
Val Lys Lys Gly Asp Ser Ala Ile Met Lys Ser Glu Leu Glu Tyr Gly
            260                 265                 270 aac tgc aac acc aag tgt caa act cca atg ggg gcg ata aac tct agt    864
Asn Cys Asn Thr Lys Cys Gln Thr Pro Met Gly Ala Ile Asn Ser Ser
        275                 280                 285 atg cca ttc cac aac ata cac cct ctc acc atc ggg gaa tgc ccc aaa    912
Met Pro Phe His Asn Ile His Pro Leu Thr Ile Gly Glu Cys Pro Lys
    290                 295                 300 tat gtg aaa tca aac aga tta gtc ctt gca aca ggg ctc aga aat agc    960
Tyr Val Lys Ser Asn Arg Leu Val Leu Ala Thr Gly Leu Arg Asn Ser
305                 310                 315                 320 cct caa aga gag agc aga aga aaa aag aga gga cta ttt gga gct ata    1008
Pro Gln Arg Glu Ser Arg Arg Lys Lys Arg Gly Leu Phe Gly Ala Ile
                325                 330                 335 gca ggt ttt ata gag gga gga tgg cag gga atg gta gat ggc tgg tat    1056
Ala Gly Phe Ile Glu Gly Gly Trp Gln Gly Met Val Asp Gly Trp Tyr
            340                 345                 350 ggg tac cac cat agc aat gag cag ggg agt ggg tac gct gca gac aaa    1104
Gly Tyr His His Ser Asn Glu Gln Gly Ser Gly Tyr Ala Ala Asp Lys
        355                 360                 365 gaa tcc act caa aag gca ata gat gga gtc acc aat aag gtc aac tca    1152
Glu Ser Thr Gln Lys Ala Ile Asp Gly Val Thr Asn Lys Val Asn Ser
    370                 375                 380 att att gac aaa atg aac act cag ttt gag gct gtt gga agg gaa ttt    1200
Ile Ile Asp Lys Met Asn Thr Gln Phe Glu Ala Val Gly Arg Glu Phe
385                 390                 395                 400 aat aac tta gaa agg aga ata gag aat tta aac aag aag atg gaa gac    1248
Asn Asn Leu Glu Arg Arg Ile Glu Asn Leu Asn Lys Lys Met Glu Asp
                405                 410                 415 ggg ttt cta gat gtt tgg act tat aat gcc gaa ctt ctg gtt ctc atg    1296
Gly Phe Leu Asp Val Trp Thr Tyr Asn Ala Glu Leu Leu Val Leu Met
            420                 425                 430 gaa aat gag aga act cta gac ttt cat gac tca aat gtt aag aac ctc    1344
Glu Asn Glu Arg Thr Leu Asp Phe His Asp Ser Asn Val Lys Asn Leu
        435                 440                 445 tac gac aag gtc cga cta cag ctt agg gat aat gca aaa gag ctg ggt    1392
Tyr Asp Lys Val Arg Leu Gln Leu Arg Asp Asn Ala Lys Glu Leu Gly
```

```
                Tyr Asp Lys Val Arg Leu Gln Leu Arg Asp Asn Ala Lys Glu Leu Gly
                    450                 455                 460 aac ggt tgt ttc gag ttc tat cac aaa tgt gat aat gaa tgt atg gaa          1440
Asn Gly Cys Phe Glu Phe Tyr His Lys Cys Asp Asn Glu Cys Met Glu
465                 470                 475                 480 agt ata aga aac gga acg tac aac tat ccg cag tat tca gaa gaa gca          1488
Ser Ile Arg Asn Gly Thr Tyr Asn Tyr Pro Gln Tyr Ser Glu Glu Ala
                485                 490                 495 aga tta aaa aga gag gaa ata agt ggg gta aaa ttg gaa tca ata gga          1536
Arg Leu Lys Arg Glu Glu Ile Ser Gly Val Lys Leu Glu Ser Ile Gly
            500                 505                 510 act tac caa ata ctg tca att tat tca aca gta gcg agt tcc cta gca          1584
Thr Tyr Gln Ile Leu Ser Ile Tyr Ser Thr Val Ala Ser Ser Leu Ala
        515                 520                 525 ctg gca atc atg ata gct ggt cta tct tta tgg atg tgc tcc aat gga          1632
Leu Ala Ile Met Ile Ala Gly Leu Ser Leu Trp Met Cys Ser Asn Gly
    530                 535                 540 tcg tta caa tgc aga att tgc att                                          1656
Ser Leu Gln Cys Arg Ile Cys Ile
545                 550

<210> SEQ ID NO 6
<211> LENGTH: 552
<212> TYPE: PRT
<213> ORGANISM: Avian influenza virus

<400> SEQUENCE: 6

Asp Gln Ile Cys Ile Gly Tyr His Ala Asn Asn Ser Thr Glu Gln Val
1               5                   10                  15

Asp Thr Ile Met Glu Lys Asn Val Thr Val Thr His Ala Gln Asp Ile
                20                  25                  30

Leu Glu Lys Thr His Asn Gly Lys Leu Cys Asp Leu Asp Gly Val Lys
            35                  40                  45

Pro Leu Ile Leu Arg Asp Cys Ser Val Ala Gly Trp Leu Leu Gly Asn
        50                  55                  60

Pro Met Cys Asp Glu Phe Ile Asn Val Pro Glu Trp Ser Tyr Ile Val
65                  70                  75                  80

Glu Lys Ala Asn Pro Thr Asn Asp Leu Cys Tyr Pro Gly Ser Phe Asn
                85                  90                  95

Asp Tyr Glu Glu Leu Lys His Leu Leu Ser Arg Ile Asn His Phe Glu
            100                 105                 110

Lys Ile Gln Ile Ile Pro Lys Ser Ser Trp Ser Asp His Glu Ala Ser
        115                 120                 125

Ser Gly Val Ser Ser Ala Cys Pro Tyr Leu Gly Ser Pro Ser Phe Phe
    130                 135                 140

Arg Asn Val Val Trp Leu Ile Lys Lys Asn Asn Ala Tyr Pro Thr Ile
145                 150                 155                 160

Lys Lys Ser Tyr Asn Asn Thr Asn Gln Glu Asp Leu Leu Val Leu Trp
                165                 170                 175

Gly Ile His His Pro Asn Asp Ala Ala Glu Gln Thr Lys Leu Tyr Gln
            180                 185                 190

Asn Pro Thr Thr Tyr Ile Ser Ile Gly Thr Ser Thr Leu Asn Gln Arg
        195                 200                 205

Leu Val Pro Lys Ile Ala Thr Arg Ser Lys Val Asn Gly Gln Ser Gly
    210                 215                 220

Arg Met Glu Phe Phe Trp Ala Ile Leu Lys Pro Asn Asp Ala Ile Asn
225                 230                 235                 240
```

-continued

```
Phe Glu Ser Asn Gly Asn Phe Ile Ala Pro Glu Tyr Ala Tyr Lys Ile
            245                 250                 255

Val Lys Lys Gly Asp Ser Ala Ile Met Lys Ser Glu Leu Glu Tyr Gly
        260                 265                 270

Asn Cys Asn Thr Lys Cys Gln Thr Pro Met Gly Ala Ile Asn Ser Ser
    275                 280                 285

Met Pro Phe His Asn Ile His Pro Leu Thr Ile Gly Glu Cys Pro Lys
290                 295                 300

Tyr Val Lys Ser Asn Arg Leu Val Leu Ala Thr Gly Leu Arg Asn Ser
305                 310                 315                 320

Pro Gln Arg Glu Ser Arg Arg Lys Lys Arg Gly Leu Phe Gly Ala Ile
                325                 330                 335

Ala Gly Phe Ile Glu Gly Gly Trp Gln Gly Met Val Asp Gly Trp Tyr
            340                 345                 350

Gly Tyr His His Ser Asn Glu Gln Gly Ser Gly Tyr Ala Ala Asp Lys
        355                 360                 365

Glu Ser Thr Gln Lys Ala Ile Asp Gly Val Thr Asn Lys Val Asn Ser
    370                 375                 380

Ile Ile Asp Lys Met Asn Thr Gln Phe Glu Ala Val Gly Arg Glu Phe
385                 390                 395                 400

Asn Asn Leu Glu Arg Arg Ile Glu Asn Leu Asn Lys Lys Met Glu Asp
                405                 410                 415

Gly Phe Leu Asp Val Trp Thr Tyr Asn Ala Glu Leu Leu Val Leu Met
            420                 425                 430

Glu Asn Glu Arg Thr Leu Asp Phe His Asp Ser Asn Val Lys Asn Leu
        435                 440                 445

Tyr Asp Lys Val Arg Leu Gln Leu Arg Asp Asn Ala Lys Glu Leu Gly
    450                 455                 460

Asn Gly Cys Phe Glu Phe Tyr His Lys Cys Asp Asn Glu Cys Met Glu
465                 470                 475                 480

Ser Ile Arg Asn Gly Thr Tyr Asn Tyr Pro Gln Tyr Ser Glu Glu Ala
                485                 490                 495

Arg Leu Lys Arg Glu Glu Ile Ser Gly Val Lys Leu Glu Ser Ile Gly
            500                 505                 510

Thr Tyr Gln Ile Leu Ser Ile Tyr Ser Thr Val Ala Ser Ser Leu Ala
        515                 520                 525

Leu Ala Ile Met Ile Ala Gly Leu Ser Leu Trp Met Cys Ser Asn Gly
    530                 535                 540

Ser Leu Gln Cys Arg Ile Cys Ile
545                 550

<210> SEQ ID NO 7
<211> LENGTH: 1707
<212> TYPE: DNA
<213> ORGANISM: Avian influenza virus
<220> FEATURE:
<221> NAME/KEY: CDS
<222> LOCATION: (1)..(1704)

<400> SEQUENCE: 7 atg gag aaa ata gtg ctt ctt ctt gca ata gtc agt ctt gtt aaa agt    48
Met Glu Lys Ile Val Leu Leu Leu Ala Ile Val Ser Leu Val Lys Ser
1               5                   10                  15 gat cag att tgc att ggt tac cat gca aac aat tca aca gag cag gtt    96
Asp Gln Ile Cys Ile Gly Tyr His Ala Asn Asn Ser Thr Glu Gln Val
            20                  25                  30
```

```
gac aca atc atg gaa aag aac gtt act gtt aca cat gcc caa gac ata      144
Asp Thr Ile Met Glu Lys Asn Val Thr Val Thr His Ala Gln Asp Ile
        35                  40                  45 ctg gaa aag aca cac aac ggg aag ctc tgc gat cta gat gga gtg aag      192
Leu Glu Lys Thr His Asn Gly Lys Leu Cys Asp Leu Asp Gly Val Lys
 50                  55                  60 cct cta att tta aga gat tgt agt gta gct gga tgg ctc ctc ggg aac      240
Pro Leu Ile Leu Arg Asp Cys Ser Val Ala Gly Trp Leu Leu Gly Asn
65                  70                  75                  80 cca atg tgt gac gaa ttc atc aat gta ccg gaa tgg tct tac ata gtg      288
Pro Met Cys Asp Glu Phe Ile Asn Val Pro Glu Trp Ser Tyr Ile Val
                85                  90                  95 gag aag gcc aat cca acc aat gac ctc tgt tac cca ggg agt ttc aac      336
Glu Lys Ala Asn Pro Thr Asn Asp Leu Cys Tyr Pro Gly Ser Phe Asn
            100                 105                 110 gac tat gaa gaa ctg aaa cat cta ttg agc aga ata aac cat ttt gag      384
Asp Tyr Glu Glu Leu Lys His Leu Leu Ser Arg Ile Asn His Phe Glu
        115                 120                 125 aaa att caa atc atc ccc aaa agt tct tgg tcc gat cat gaa gcc tca      432
Lys Ile Gln Ile Ile Pro Lys Ser Ser Trp Ser Asp His Glu Ala Ser
130                 135                 140 tca gga gtg agc tca gca tgt cca tac ctg gga agt ccc tcc ttt ttt      480
Ser Gly Val Ser Ser Ala Cys Pro Tyr Leu Gly Ser Pro Ser Phe Phe
145                 150                 155                 160 aga aat gtg gta tgg ctt atc aaa aag aac aat gca tac cca aca ata      528
Arg Asn Val Val Trp Leu Ile Lys Lys Asn Asn Ala Tyr Pro Thr Ile
                165                 170                 175 aag aaa agc tac aat aat acc aac caa gaa gat ctt ttg gta ctg tgg      576
Lys Lys Ser Tyr Asn Asn Thr Asn Gln Glu Asp Leu Leu Val Leu Trp
            180                 185                 190 gga att cac cat cct aat gat gcg gca gag cag aca aag cta tat caa      624
Gly Ile His His Pro Asn Asp Ala Ala Glu Gln Thr Lys Leu Tyr Gln
        195                 200                 205 aac cca acc acc tat att tcc att ggg aca tca aca cta aac cag aga      672
Asn Pro Thr Thr Tyr Ile Ser Ile Gly Thr Ser Thr Leu Asn Gln Arg
210                 215                 220 ttg gta cca aaa ata gct act aga tcc aaa gta aac ggg caa agt gga      720
Leu Val Pro Lys Ile Ala Thr Arg Ser Lys Val Asn Gly Gln Ser Gly
225                 230                 235                 240 agg atg gag ttc ttc tgg gca att tta aaa cct aat gat gca atc aac      768
Arg Met Glu Phe Phe Trp Ala Ile Leu Lys Pro Asn Asp Ala Ile Asn
                245                 250                 255 ttc gag agt aat gga aat ttc att gct cca gaa tat gca tac aaa att      816
Phe Glu Ser Asn Gly Asn Phe Ile Ala Pro Glu Tyr Ala Tyr Lys Ile
            260                 265                 270 gtc aag aaa ggg gac tca gca att atg aaa agt gaa ttg gaa tat ggt      864
Val Lys Lys Gly Asp Ser Ala Ile Met Lys Ser Glu Leu Glu Tyr Gly
        275                 280                 285 aac tgc aac acc aag tgt caa act cca atg ggg gcg ata aac tct agt      912
Asn Cys Asn Thr Lys Cys Gln Thr Pro Met Gly Ala Ile Asn Ser Ser
290                 295                 300 atg cca ttc cac aac ata cac cct ctc acc atc ggg gaa tgc ccc aaa      960
Met Pro Phe His Asn Ile His Pro Leu Thr Ile Gly Glu Cys Pro Lys
305                 310                 315                 320 tat gtg aaa tca aac aga tta gtc ctt gca aca ggg ctc aga aat agc     1008
Tyr Val Lys Ser Asn Arg Leu Val Leu Ala Thr Gly Leu Arg Asn Ser
                325                 330                 335 cct caa aga gag agc aga aga aaa aag aga gga cta ttt gga gct ata     1056
Pro Gln Arg Glu Ser Arg Arg Lys Lys Arg Gly Leu Phe Gly Ala Ile
```

```
                       340             345             350
gca ggt ttt ata gag gga gga tgg cag gga atg gta gat ggc tgg tat    1104
Ala Gly Phe Ile Glu Gly Gly Trp Gln Gly Met Val Asp Gly Trp Tyr
        355             360             365 ggg tac cac cat agc aat gag cag ggg agt ggg tac gct gca gac aaa    1152
Gly Tyr His His Ser Asn Glu Gln Gly Ser Gly Tyr Ala Ala Asp Lys
370             375             380 gaa tcc act caa aag gca ata gat gga gtc acc aat aag gtc aac tca    1200
Glu Ser Thr Gln Lys Ala Ile Asp Gly Val Thr Asn Lys Val Asn Ser
385             390             395             400 att att gac aaa atg aac act cag ttt gag gct gtt gga agg gaa ttt    1248
Ile Ile Asp Lys Met Asn Thr Gln Phe Glu Ala Val Gly Arg Glu Phe
        405             410             415 aat aac tta gaa agg aga ata gag aat tta aac aag aag atg gaa gac    1296
Asn Asn Leu Glu Arg Arg Ile Glu Asn Leu Asn Lys Lys Met Glu Asp
            420             425             430 ggg ttt cta gat gtt tgg act tat aat gcc gaa ctt ctg gtt ctc atg    1344
Gly Phe Leu Asp Val Trp Thr Tyr Asn Ala Glu Leu Leu Val Leu Met
        435             440             445 gaa aat gag aga act cta gac ttt cat gac tca aat gtt aag aac ctc    1392
Glu Asn Glu Arg Thr Leu Asp Phe His Asp Ser Asn Val Lys Asn Leu
450             455             460 tac gac aag gtc cga cta cag ctt agg gat aat gca aaa gag ctg ggt    1440
Tyr Asp Lys Val Arg Leu Gln Leu Arg Asp Asn Ala Lys Glu Leu Gly
465             470             475             480 aac ggt tgt ttc gag ttc tat cac aaa tgt gat aat gaa tgt atg gaa    1488
Asn Gly Cys Phe Glu Phe Tyr His Lys Cys Asp Asn Glu Cys Met Glu
        485             490             495 agt ata aga aac gga acg tac aac tat ccg cag tat tca gaa gaa gca    1536
Ser Ile Arg Asn Gly Thr Tyr Asn Tyr Pro Gln Tyr Ser Glu Glu Ala
            500             505             510 aga tta aaa aga gag gaa ata agt ggg gta aaa ttg gaa tca ata gga    1584
Arg Leu Lys Arg Glu Glu Ile Ser Gly Val Lys Leu Glu Ser Ile Gly
        515             520             525 act tac caa ata ctg tca att tat tca aca gta gcg agt tcc cta gca    1632
Thr Tyr Gln Ile Leu Ser Ile Tyr Ser Thr Val Ala Ser Ser Leu Ala
530             535             540 ctg gca atc atg ata gct ggt cta tct tta tgg atg tgc tcc aat gga    1680
Leu Ala Ile Met Ile Ala Gly Leu Ser Leu Trp Met Cys Ser Asn Gly
545             550             555             560 tcg tta caa tgc aga att tgc att taa                                1707
Ser Leu Gln Cys Arg Ile Cys Ile
                565

<210> SEQ ID NO 8
<211> LENGTH: 568
<212> TYPE: PRT
<213> ORGANISM: Avian influenza virus

<400> SEQUENCE: 8

Met Glu Lys Ile Val Leu Leu Leu Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
```

-continued

```
                65                  70                  75                  80
Pro Met Cys Asp Glu Phe Ile Asn Val Pro Glu Trp Ser Tyr Ile Val
                        85                  90                  95
Glu Lys Ala Asn Pro Thr Asn Asp Leu Cys Tyr Pro Gly Ser Phe Asn
                        100                 105                 110
Asp Tyr Glu Glu Leu Lys His Leu Leu Ser Arg Ile Asn His Phe Glu
                        115                 120                 125
Lys Ile Gln Ile Ile Pro Lys Ser Ser Trp Ser Asp His Glu Ala Ser
                        130                 135                 140
Ser Gly Val Ser Ser Ala Cys Pro Tyr Leu Gly Ser Pro Ser Phe Phe
145                 150                 155                 160
Arg Asn Val Val Trp Leu Ile Lys Lys Asn Asn Ala Tyr Pro Thr Ile
                        165                 170                 175
Lys Lys Ser Tyr Asn Asn Thr Asn Gln Glu Asp Leu Leu Val Leu Trp
                        180                 185                 190
Gly Ile His His Pro Asn Asp Ala Ala Glu Gln Thr Lys Leu Tyr Gln
                        195                 200                 205
Asn Pro Thr Thr Tyr Ile Ser Ile Gly Thr Ser Thr Leu Asn Gln Arg
            210                 215                 220
Leu Val Pro Lys Ile Ala Thr Arg Ser Lys Val Asn Gly Gln Ser Gly
225                 230                 235                 240
Arg Met Glu Phe Phe Trp Ala Ile Leu Lys Pro Asn Asp Ala Ile Asn
                        245                 250                 255
Phe Glu Ser Asn Gly Asn Phe Ile Ala Pro Glu Tyr Ala Tyr Lys Ile
                        260                 265                 270
Val Lys Lys Gly Asp Ser Ala Ile Met Lys Ser Glu Leu Glu Tyr Gly
                275                 280                 285
Asn Cys Asn Thr Lys Cys Gln Thr Pro Met Gly Ala Ile Asn Ser Ser
            290                 295                 300
Met Pro Phe His Asn Ile His Pro Leu Thr Ile Gly Glu Cys Pro Lys
305                 310                 315                 320
Tyr Val Lys Ser Asn Arg Leu Val Leu Ala Thr Gly Leu Arg Asn Ser
                    325                 330                 335
Pro Gln Arg Glu Ser Arg Arg Lys Lys Arg Gly Leu Phe Gly Ala Ile
                    340                 345                 350
Ala Gly Phe Ile Glu Gly Gly Trp Gln Gly Met Val Asp Gly Trp Tyr
                355                 360                 365
Gly Tyr His His Ser Asn Glu Gln Gly Ser Gly Tyr Ala Ala Asp Lys
            370                 375                 380
Glu Ser Thr Gln Lys Ala Ile Asp Gly Val Thr Asn Lys Val Asn Ser
385                 390                 395                 400
Ile Ile Asp Lys Met Asn Thr Gln Phe Glu Ala Val Gly Arg Glu Phe
                    405                 410                 415
Asn Asn Leu Glu Arg Arg Ile Glu Asn Leu Asn Lys Lys Met Glu Asp
                    420                 425                 430
Gly Phe Leu Asp Val Trp Thr Tyr Asn Ala Glu Leu Leu Val Leu Met
                435                 440                 445
Glu Asn Glu Arg Thr Leu Asp Phe His Asp Ser Asn Val Lys Asn Leu
            450                 455                 460
Tyr Asp Lys Val Arg Leu Gln Leu Arg Asp Asn Ala Lys Glu Leu Gly
465                 470                 475                 480
Asn Gly Cys Phe Glu Phe Tyr His Lys Cys Asp Asn Glu Cys Met Glu
                    485                 490                 495
```

-continued

```
Ser Ile Arg Asn Gly Thr Tyr Asn Tyr Pro Gln Tyr Ser Glu Ala
            500                 505                 510

Arg Leu Lys Arg Glu Glu Ile Ser Gly Val Lys Leu Glu Ser Ile Gly
        515                 520                 525

Thr Tyr Gln Ile Leu Ser Ile Tyr Ser Thr Val Ala Ser Ser Leu Ala
    530                 535                 540

Leu Ala Ile Met Ile Ala Gly Leu Ser Leu Trp Met Cys Ser Asn Gly
545                 550                 555                 560

Ser Leu Gln Cys Arg Ile Cys Ile
                565

<210> SEQ ID NO 9
<211> LENGTH: 12
<212> TYPE: PRT
<213> ORGANISM: Avian influenza virus

<400> SEQUENCE: 9

Glu Phe Ile Asn Val Pro Glu Trp Ser Tyr Ile Val
1               5                   10

<210> SEQ ID NO 10
<211> LENGTH: 48
<212> TYPE: PRT
<213> ORGANISM: Avian influenza virus

<400> SEQUENCE: 10

Ile Ile Pro Lys Ser Ser Trp Ser Asp His Glu Ala Ser Ser Gly Val
1               5                   10                  15

Ser Ser Ala Cys Pro Tyr Gln Gly Arg Ser Ser Phe Phe Arg Asn Val
            20                  25                  30

Val Trp Leu Ile Lys Lys Asn Asn Thr Tyr Pro Thr Ile Lys Arg Ser
        35                  40                  45

<210> SEQ ID NO 11
<211> LENGTH: 78
<212> TYPE: PRT
<213> ORGANISM: Avian influenza virus

<400> SEQUENCE: 11

Ser Tyr Asn Asn Thr Asn Gln Glu Asp Leu Leu Val Leu Trp Gly Ile
1               5                   10                  15

His His Pro Asn Asp Ala Ala Glu Gln Thr Arg Leu Tyr Gln Asn Pro
            20                  25                  30

Thr Thr Tyr Ile Ser Val Gly Thr Ser Thr Leu Asn Gln Arg Leu Val
        35                  40                  45

Pro Lys Ile Ala Thr Arg Ser Lys Val Asn Gly Gln Ser Gly Arg Met
    50                  55                  60

Glu Phe Phe Trp Thr Ile Leu Lys Pro Asn Asp Ala Ile Asn
65                  70                  75
```

MONOVALENT H5 VACCINE

CROSS-REFERENCE TO RELATED APPLICATION

The present application is a U.S. National Phase Entry of PCT/SG2014/000594, filed 12 Dec. 2014, which in turn is related to and claims priority to U.S. provisional patent application Ser. No. 61/920,187 filed 23 Dec. 2013. Each application is incorporated herein by reference.

SEQUENCE SUBMISSION

The present application is being filed along with a Sequence Listing in electronic format. The Sequence Listing is entitled 2577234PCTSequenceListing.txt, created on 4 Dec. 2014 and is 53 kb in size. The information in the electronic format of the Sequence Listing is incorporated herein by reference in its entirety.

BACKGROUND OF THE INVENTION

The present invention relates to a monovalent H5N1 vaccine. More specifically, the present invention relates to the development of a monovalent H5 vaccine strain using hemagglutinin (HA) engineering to elicit cross-clade protection. The present invention also relates to an epitope-chimeric H5 and to a reverse genetics (RG) influenza virus expressing the epitope-chimeric H5.

The publications and other materials used herein to illuminate the background of the invention or provide additional details respecting the practice, are incorporated by reference, and for convenience are respectively grouped in the Bibliography.

Recurrence of highly pathogenic avian influenza (HPAI) virus subtype H5N1 in humans and poultry continues to be a serious concern to public health. Since their emergence in Asia over a decade ago, highly pathogenic avian influenza H5N1 viruses have spread to over sixty countries on three continents and are endemic among poultry in South East Asia and Africa (Peiris et al., 2007). It has caused disease in several mammals, including humans, often with lethal consequence. Up to date, H5N1 has resulted in 641 human cases worldwide, including 380 deaths (http, 2013). Although so far no sustained human to human transmission of the virus has been observed, the concern remains that, if human transmissibility was acquired, a severe pandemic could result (Guan et al., 2004; Imai et al., 2012).

Vaccination remains the most effective and economically prudent strategy to combat the threat posed by avian influenza viruses with pandemic potential (Baz et al. 2013). However, it will be a challenge to produce an effective vaccine if a pandemic comes up suddenly and spreads rapidly. Therefore, efforts are being undertaken to develop pandemic vaccines that use less antigen and induce cross-protective responses. The highly conserved ion channel protein (M2) (Wu et al., 2007) and the nucleoprotein (NP) of influenza virus have been evaluated for the induction of cross-protective cellular immunity and viral clearance (Chen and Subbarao, 2009). However, antibodies specific to these proteins are poorly immunogenic and infection permissive. Thus, the development of a vaccine based on influenza virus hemagglutinin (HA), the principal determinant of immunity to influenza virus, remains to be the most favorable option to prevent infections by HPAI influenza viruses (Gambotto et al., 2008). H5N1 viruses are antigenically distinguishable owing to differences in hemagglutinin sequences, resulting in different lineages or clades of H5N1 (Aubin et al., 2005; WHO et al., 2008). Due to variations in the HA sequences, particularly within the neutralizing epitope region, conventional HA based H5N1 vaccines appear not to be effective against heterologous strains or phylogenetically variant clades of H5N1 (Shore et al., 2013). Hence, the strategy to exploit a cocktail of antigenically different triple or more virus strains was developed to elicit broad protection. However, either the propagation of individual vaccine seed viruses or the development of co-expression recombinant vaccines is time-consuming, technique-demanding and expensive.

Therefore, it is important to develop a prepandemic monovalent vaccine that induces cross-clade protection against antigenically distinct H5N1 strains.

SUMMARY OF THE INVENTION

The present invention relates to a monovalent H5N1 vaccine. More specifically, the present invention relates to the development of a monovalent H5 vaccine strain using hemagglutinin (HA) engineering to elicit cross-clade protection. The present invention also relates to an epitope-chimeric H5 and to a reverse genetics (RG) influenza virus expressing the epitope-chimeric H5.

Thus, in a first aspect, the present invention provides a modified H5 protein, an isolated modified H5 protein or a purified modified H5 protein of a strain of avian influenza virus. In one embodiment, the strain of avian influenza virus is A/Indonesia/CDC669/2006 (H5N1). The native, full-length H5 protein of this strain is set forth in GenBank Accession No. ABI36428 and is encoded by a nucleic acid having the nucleotide sequence set forth in GenBank Accession No. CY014481. The nucleotide sequence of this nucleic acid is set forth in SEQ ID NO:1. The amino acid sequence of the native, full-length H5 protein of this strain is set forth in SEQ ID NO:2. The native, mature H5 protein (i.e., the H5 protein lacking the signal peptide) of this strain is encoded by a nucleic acid having the nucleotide sequence set forth in SEQ ID NO:3. The amino acid sequence of the native, mature H5 protein is set forth in SEQ ID NO:4. In one embodiment, the modified, mature H5 protein has the modifications S155N, T156A and R189K. These modifications correspond to the modifications at residues 171, 172 and 205, respectively in the full-length H5 protein. The amino acid sequence of the modified, mature H5 protein is set forth in SEQ ID NO:6 which is encoded by a nucleic acid having the nucleotide sequence set forth in SEQ ID NO:5. The amino acid sequence of the modified, full-length H5 protein is set forth in SEQ ID NO:8 which is encoded by a nucleic acid having the nucleotide sequence set forth in SEQ ID NO:7. The modified H5 is also sometimes referred to herein as an epitope-chimeric H5 (EC H5).

In a second aspect, the present invention provides a recombinant avian influenza virus comprising the modified H5 protein described herein. The recombinant avian influenza virus may include the modified H5 protein in the genetic background of an avian influenza virus. The avian influenza virus may be a master strain virus. In one embodiment, the recombinant avian influenza virus may be used as a vaccine. The recombinant avian influenza virus may be included in an immunization kit. In another embodiment, the recombinant avian influenza virus may be used as a diagnostic reference virus in a hemagglutinin inhibition (HI) assay. The recombinant avian influenza virus may be included in a hemagglutinin inhibition (HI) assay kit. In some embodiments, the recombinant avian influenza virus is produced by a reverse genetics process.

In a third aspect, the present invention provides a monovalent H5 vaccine for the prevention of a disease in a subject, wherein the disease is associated with an H5N1 subtype of avian influenza virus. In accordance with this aspect, the monovalent H5 vaccine comprises a prophylactically effective amount of an immunogenic agent. In one embodiment, the immunogenic agent comprises a modified H5 protein described herein or antigenic portion thereof or a nucleic acid encoding the modified H5 protein described herein or antigenic portion thereof. In an additional embodiment, the antigenic portion includes an epitope of the modified H5 protein described herein. In a further embodiment, the subjects may be humans, domestic animals (dog, cat, monkey etc.); livestock (horse, cow, sheep, goat, pig etc.), wild birds (wild geese, wild ducks, etc.) and domestic birds (chicken, duck, geese etc.). In one embodiment, the immunogenic agent is virus comprising the modified H5 protein described herein or is a recombinant virus as described herein. In another embodiment, the virus or recombinant virus is inactivated. In an additional embodiment, the virus or recombinant virus is an attenuated virus. In another embodiment, the virus or recombinant virus is in the form of a virosome or a virus-like particle. In a further embodiment, the virus or recombinant virus is egg-derived or cell culture-derived. In another embodiment, the immunogenic agent is a split virus comprising the modified H5 protein described herein or a split virus antigenic preparation. In one embodiment, the immunogenic agent is the modified H5 protein or antigenic portion thereof. In another embodiment, the modified H5 protein or antigenic portion thereof has been isolated. In an additional embodiment, the modified H5 protein or antigenic portion thereof is produced by an expression system. In one embodiment, the expression system is any expression system, such as a viral expression vector in which the modified H5 protein or antigenic portion thereof is presented or displayed on the surface of the virus. In one embodiment, the viral expression vector is any viral expression vector such as a modified vaccinia virus expression vector, an adenovirus expression vector, a poxvirus expression vector, a baculovirus expression vector and the like. In one embodiment, the expression vector is a baculovirus expression vector and the virus presenting or displaying the modified H5 protein or antigenic portion thereof is a baculovirus. In another embodiment, the immunogenic agent is a nucleic acid encoding the modified H5 protein or antigenic portion thereof which is capable of expression in the subject.

In a fourth aspect, the present invention provides a method for producing protective immunity to an avian influenza virus which comprises administering to a subject a prophylactically effective amount of a monovalent H5 vaccine described herein.

In a fifth aspect, the present invention provides a method for the prevention or treatment of a disease associated with an avian influenza virus which comprises administering to a subject a prophylactically effective amount of a monovalent H5 vaccine described herein. In one embodiment, the prevention or treatment delays the onset of or slows the rate of progression of avian influenza.

In a sixth aspect, the present invention provides use of a monovalent H5 vaccine described herein for stimulating an immune response to an avian influenza virus.

In a seventh aspect, the present invention provides a use of a recombinant avian influenza virus described herein for the manufacture of a medicament for eliciting a protective immune response in a subject.

In an eighth aspect, the present invention provides a use of a recombinant avian influenza virus described herein for the manufacture of a medicament for preventing a subject from becoming afflicted with H5N1 subtype avian influenza.

In a ninth aspect, the present invention provides a use of a recombinant avian influenza virus described herein for the manufacture of a medicament for delaying the onset of or slowing the rate of H5N1 subtype avian influenza in an H5N1 avian influenza-infected subject.

In a tenth aspect, the present invention provides a method of making a vaccine comprising using the modified H5 protein described herein or the recombinant avian influenza virus described herein.

In an eleventh aspect, the present invention provides a use of the modified H5 protein described herein or of the recombinant avian influenza virus described herein, for vaccine development.

In a twelfth aspect, the present invention provides a modified H5 protein described herein or a recombinant avian influenza virus described herein for use in vaccine development

BRIEF DESCRIPTION OF THE FIGURES

Figure 1A:
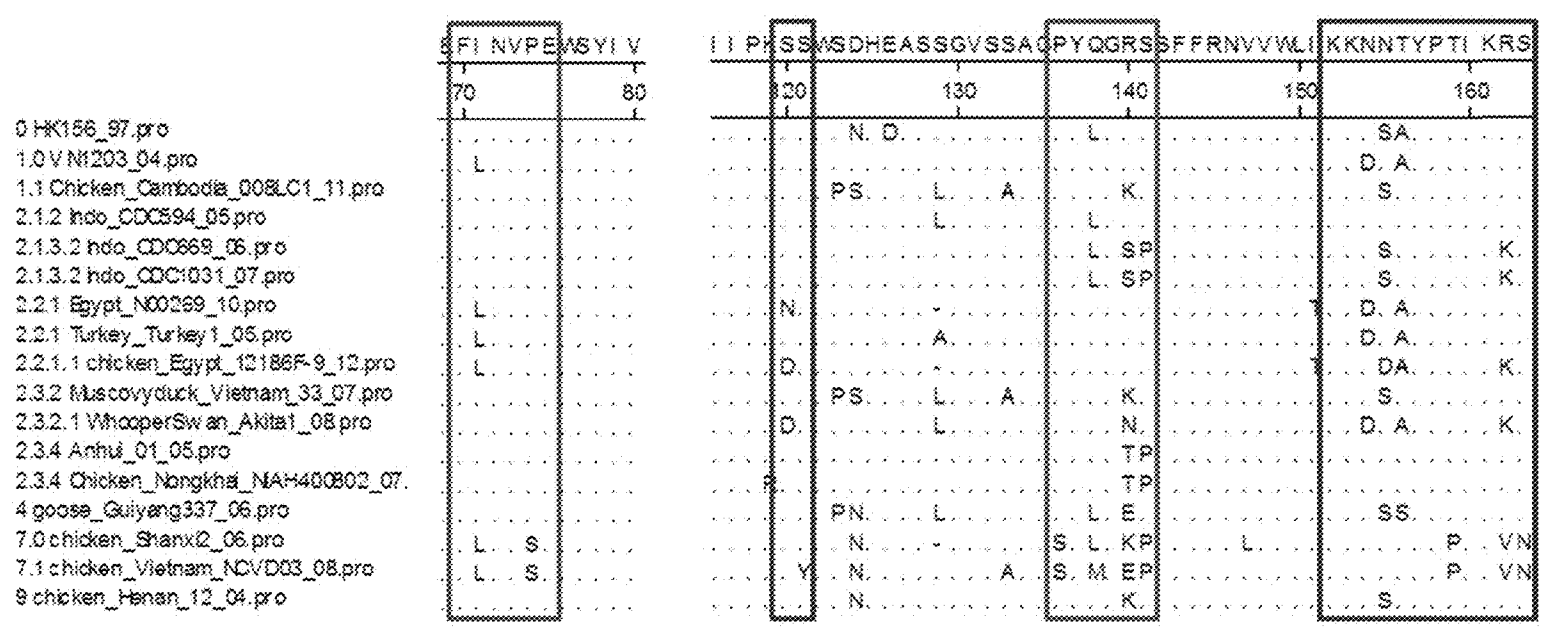

FIGS. 1A and 1B show the identification of variable amino acids in antigenic epitopes among different clades. H5 protein sequences of different major clades were aligned. Amino acid consensus sequences (SEQ ID NO:3, SEQ ID NO:4 and SEQ ID NO:5) of H5N1 HA clades were highlighted at positions equivalent to the H1 antigenic sites, Ca (in boxes at amino acid residues 136-141, 165-169, 202-204, 220-221 and 234-236), Cb (in box at amino acid residues 69-75), Sa (in boxes at amino acid residues 120-121 and 152-163) and Sb (in box at 183-194). FIG. 2A: HI titer against different clades of H5N1s. FIG. 2B: Virus neutralization titer against different clades of H5N1s. Clade number was listed before each virus name accordingly. Each point represents the arithmetic mean value (n=10)±SD.

FIG. 4 shows the histopathology of lung tissue in vaccinated mice. Shown are photomicrographs of hematoxylin- and eosin-stained lung sections of mice 5 days after challenge with clade 2.3.4 A/Anhui/1/05 or clade 2.2.1.1 A/Egypt/3300-NAMRU3/2008 H5N1 strains. Mice were immunized with RG-EC H5, A/Vietnam/1203/2004, A/Indonesia/CDC669/2006 or PBS respectively. The immunization strain and challenge strain were shown accordingly.

FIG. 5 shows the measurement of viral infectivity titers in the lungs of vaccinated mice. Mice were subcutaneously immunized with RG-EC H5, A/Vietnam/1203/2004, A/Indonesia/CDC669/2006 or PBS respectively. Lung samples were collected from mice 5 days after challenge with 5 MLD50 of clade 1.0 (A/Vietnam/1203/2004), clade 2.1 A/Indonesia/CDC669/2006, clade 2.3.4 A/Anhui/1/05 or clade 2.2.1.1 A/Egypt/3300-NAMRU3/2008. The results of virus load in lungs were expressed in terms of mean value of $\log_{10} TCID_{50}$. Each point represents the arithmetic mean value (n=2)±SD.

DETAILED DESCRIPTION OF THE INVENTION

Figure 1B:
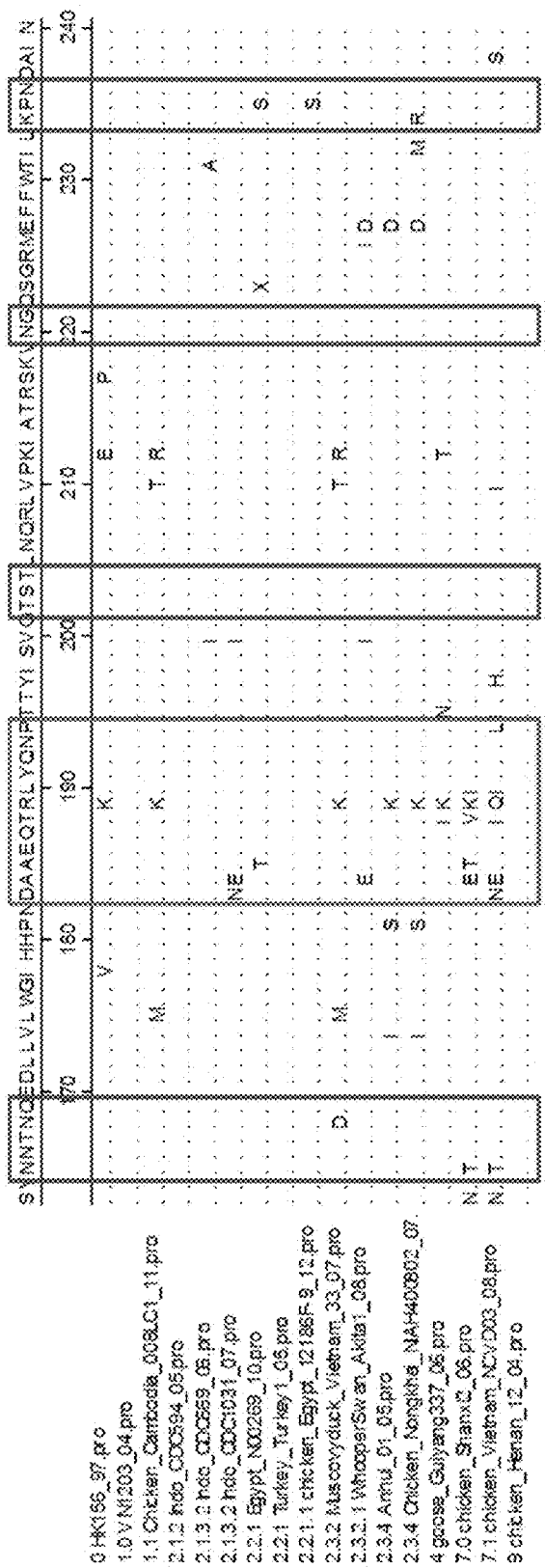

The present invention relates to a monovalent H5N1 vaccine. More specifically, the present invention relates to the development of a monovalent H5 vaccine strain using hemagglutinin (HA) engineering to elicit cross-clade protection. The present invention also relates to an epitope-chimeric H5 and to a reverse genetics (RG) influenza virus expressing the epitope-chimeric H5.

Unless defined otherwise, all technical and scientific terms used herein have the same meaning as is commonly understood by one of skill in the art to which the invention belongs.

The term "about" or "approximately" means within a statistically meaningful range of a value. Such a range can be within an order of magnitude, preferably within 50%, more preferably within 20%, more preferably still within 10%, and even more preferably within 5% of a given value or range. The allowable variation encompassed by the term "about" or "approximately" depends on the particular system under study, and can be readily appreciated by one of ordinary skill in the art.

The term "adjuvant" refers to a compound or mixture that enhances the immune response to an antigen. An adjuvant can serve as a tissue depot that slowly releases the antigen and also as a lymphoid system activator that non-specifically enhances the immune response (Hood, et al., 1984). Often, a primary challenge with an antigen alone, in the absence of an adjuvant, will fail to elicit a humoral or cellular immune response. Adjuvants include, but are not limited to, complete Freund's adjuvant, incomplete Freund's adjuvant, saponin, mineral gels such as aluminum hydroxide, surface active substances such as lysolecithin, pluronic polyols, polyanions, peptides, oil or hydrocarbon emulsions, keyhole limpet hemocyanins, and potentially useful human adjuvants such as N-acetyl-muramyl-L-threonyl-D-isoglutamine (thr-MDP), N-acetyl-nor-muramyl-L-alanyl-D-isoglutamine, N-acetylmuramyl-L-alanyl-D-isoglutaminyl-L-alanine-2-(1'-2'-dipalmitoyl-s-n-glycero-3-hydroxyphosphoryloxy)-ethylamine, BCG (bacille Calmette-Guerin) and *Corynebacterium parvum*. Preferably, the adjuvant is pharmaceutically acceptable.

As used herein, "administering" means delivering using any of the various methods and delivery systems known to those skilled in the art. Administering can be performed, for example, intraperitoneally, intracerebrally, intravenously, orally, transmucosally, subcutaneously, transdermally, intradermally, intramuscularly, topically, parenterally, via implant, intrathecally, intralymphatically, intralesionally, pericardially, or epidurally. An agent or composition may also be administered in an aerosol, such as for pulmonary and/or intranasal delivery. Administering may be performed, for example, once, a plurality of times, and/or over one or more extended periods.

The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in *Remington: The Science and Practice of Pharmacy*, 21st Ed., Ed. D. B. Troy, Lippincott, Williams & Wilkins, Baltimore, 2006, hereby incorporated by reference herein.

As used herein, the phrase "disease associated with an H5N1 subtype avian influenza virus" means any disease, disease state or disorder caused by or associated with an H5N1 subtype avian influenza virus.

As used herein the term "effective amount" or a "prophylactically effective amount" includes within its meaning a non-toxic but sufficient amount of an agent or compound to provide the desired effect. For example, a prophylactically effective amount for modulating an immune response is an amount of the agent or compound that provides the desired effect of modulating the immune response in the subject. Similarly, a prophylactically effective amount for treating or preventing a disease associated with an avian influenza virus is an amount of the agent or compound that provides the desired effect of treating or preventing the disease in the subject. The exact amount required will vary from subject to subject depending on factors such as the species being treated, the age and general condition of the subject, the severity of the condition being treated, the particular agent being administered and the mode of administration and so forth. Thus, it is not possible to specify an exact "effective amount." However, for any given case, an appropriate "effective amount" may be determined by one of ordinary skill in the art using only routine experimentation.

The term "hemagglutinin 5 (H5)" or "H5 of avian influenza virus" or "H5 protein" as used herein refers to a naturally occurring H5 protein of A/Indonesia/CDC669/2006 (H5N1).

The term "modified hemagglutinin 5" or "modified H5 of avian influenza virus" or "modified H5" or "epitope-chimeric H5" refers to the H5 protein of A/Indonesia/CDC669/2006 (H5N1) modified to contain the modifications S155N, T156A and R189K.

The numbering of the amino acid positions of the H5 protein as used herein refers to the amino acid position as exemplarily given in SEQ ID NO:4. SEQ ID NO:4 represents the amino sequence of the hemagglutinin of strain A/Indonesia/CDC669/2006 (H5N1) but lacking the amino terminal signal peptide. In other words, if reference is made to the amino acid at position 155 (amino acid 155), the amino acid residue is meant which corresponds to amino acid 155 of SEQ ID NO:4. The terms "S155N" or "T156A" or "R189K" exemplarily mean, that the amino acid at positions 155, 156 and 189, respectively—numbering according to the amino acid positions of SEQ ID NO: 4—, are the amino acid asparagine (N) instead of the native Serine (S), at amino acid 155, Alanine (A) instead of the native Threonine (T) at amino acid 156 and Lysine (K) instead of the native Arginine (R) at amino acid 189.

An "immunogenic composition" or an "immunological composition" refers to a composition of matter that comprises at least one antigen which elicits an immunological response in the host of a cellular and/or antibody-mediated immune response to the composition or vaccine of interest. Usually, an "immunological response" includes but is not limited to one or more of the following effects: the production or activation of antibodies, B cells, helper T cells, suppressor T cells, and/or cytotoxic T cells and/or gamma-delta T cells, directed specifically to an antigen or antigens included in the composition or vaccine of interest. Preferably, the host will display either a therapeutic or protective immunological response such that resistance to new infection will be enhanced and/or the clinical severity of the disease reduced. Such protection will be demonstrated by either a reduction or lack of symptoms normally displayed by an infected host, a quicker recovery time and/or a lowered viral titer in the infected host.

An "individual" or "subject" or "animal", as used herein, refers to vertebrates that support a negative strand RNA virus infection, specifically influenza virus infection, including, but not limited to, birds (such as water fowl and chickens) and members of the mammalian species, such as canine, feline, lupine, mustela, rodent (racine, murine, etc.), equine, bovine, ovine, caprine, porcine species, and primates, the latter including humans. In one embodiment, the subject is a human.

The term "isolated" means that the referenced material is removed from its native environment, e.g., a cell or virus. Thus, an isolated biological material can be free of some or all cellular components, i.e., components of the cells in which the native material occurs naturally (e.g., cytoplasmic or membrane component). A material shall be deemed isolated if it is present in a cell extract or supernatant. In the case of nucleic acid molecules, an isolated nucleic acid includes a PCR product, an isolated mRNA, a cDNA, or a restriction fragment. In another embodiment, an isolated nucleic acid is preferably excised from the chromosome in which it may be found, and more preferably is no longer joined or proximal to non-coding regions (but may be joined to its native regulatory regions or portions thereof), or to other genes, located upstream or downstream of the gene contained by the isolated nucleic acid molecule when found in the chromosome. In yet another embodiment, the isolated nucleic acid lacks one or more introns. Isolated nucleic acid molecules include sequences inserted into plasmids, cosmids, artificial chromosomes, and the like, i.e., when it forms part of a chimeric recombinant nucleic acid construct. Thus, in a specific embodiment, a recombinant nucleic acid is an isolated nucleic acid. An isolated protein may be associated with other proteins or nucleic acids, or both, with which it associates in the cell, or with cellular membranes if it is a membrane-associated protein. An isolated organelle, cell, or tissue is removed from the anatomical site in which it is found in an organism. An isolated material may be, but need not be, purified.

The term "master strain virus" refers to a viral strain is used in the construction of high growth or attenuated vaccine strains. These master strains typically contribute six gene segments to the vaccine virus (PB1, PB2, PA, NP, NA, M and NS). The master strain virus may be a strain that is also in use as a vaccine component, including virus strain A/PR/8/34.

As used herein, the term "modulating" when used in relation to an immune response means increasing or decreasing, either directly or indirectly, an immune response against an antigen. A vaccine typically increases the immune response against an antigen.

The phrase "pharmaceutically acceptable" refers to molecular entities and compositions that are physiologically tolerable and do not typically produce an allergic or similar untoward reaction, such as gastric upset, dizziness and the like, when administered to a human.

As used herein, the terms "polynucleotide" or "nucleic acid" are used interchangeably and designate a molecule comprising one or more nucleotides, or an oligonucleotide, or a fragment thereof, including but not limited to RNA or DNA nucleotides or combinations thereof.

The term "polypeptide" refers to a polymer of amino acids and does not refer to a specific length of the product; thus, peptides, oligopeptides, and proteins are included within the definition of polypeptide. This term also does not refer to, or exclude, post-translational modifications of the polypeptide, for example, glycosylations, acetylations, phosphorylations, and the like.

The term "purified" as used herein refers to material that has been isolated under conditions that reduce or eliminate the presence of unrelated materials, i.e., contaminants, including native materials from which the material is obtained. For example, a purified virion is preferably substantially free of host cell or culture components, including tissue culture or egg proteins, non-specific pathogens, and the like. As used herein, the term "substantially free" is used operationally, in the context of analytical testing of the material. Preferably, purified material substantially free of contaminants is at least about 50% pure; more preferably, at least about 90% pure, and more preferably still at least about 99% pure. Purity can be evaluated by chromatography, gel electrophoresis, immunoassay, composition analysis, biological assay, and other methods known in the art.

Methods for purification are well-known in the art. Viral particles can be purified by ultrafiltration or ultracentrifugation, preferably continuous centrifugation. Other purification methods are possible and contemplated herein. A purified material may contain less than about 50%, preferably less than about 75%, and most preferably less than about 90%, of the cellular components, media, proteins, or other nondesirable components or impurities (as context requires), with which it was originally associated. The term "substantially pure" indicates the highest degree of purity which can be achieved using conventional purification techniques known in the art.

The term "reverse genetics system" as used herein refers to methods of generating influenza virus particles, polypeptides, virons or nucleic acids by genetic engineering methods. These methods include but are not limited to the "plasmid system" as described by Hoffmann (2002), U.S. Patent Application Publication No. 2002/0164770 and U.S. Pat. No. 8,293,247, each of which is hereby incorporated by reference in its entirety. Generally speaking, reverse genetics systems allow for the creation of virus particles, polypeptides, and/or nucleic acids with specific sequences by genetic engineering methods known to those of skill in the art.

The term "therapeutically effective amount" refers to the amount of an agent which, when administered to a human or animal, which is sufficient to result in a therapeutic effect in said human or animal. The effective amount is readily determined by one of skill in the art following routine procedures.

As used herein the terms "treating" and "treatment" refer to any and all uses which remedy a condition or symptoms, prevent the establishment of a condition or disease, or otherwise prevent, hinder, retard, ameliorate or reverse the progression of a condition or disease or other undesirable symptoms in any way whatsoever.

As shown herein, a monovalent H5 vaccine strain was developed based on HA sequence engineering to elicit cross-clade protection. H5 from Indonesia strain (A/Indonesia/CDC669/2006) was used as backbone sequence. Three amino acids were mutated to express immunogenic epitopes from other circulating H5N1s in the backbone. Reverse genetics (RG) influenza virus expressing the epitope-chimeric H5 can be neutralized with multiple H5 monoclonal antibodies which fail to neutralize wild type A/Indonesia/CDC669/2006 (H5N1). High titers in HI and virus neutralization against different clades H5N1s were detected using sera from mice immunized with the epitope-chimeric H5N1. The monovalent vaccine with RG-epitope-chimeric H5N1 protected mice from lethal challenge with H5N1s of different clades, including the three strains from a trivalent universal H5 vaccine. These results indicate that the broad immune response elicited by this single H5N1 virus enables this single virus to be useful as a monovalent H5 universal vaccine.

Thus, in a first aspect, the present invention provides a modified H5 protein, an isolated modified H5 protein or a purified modified H5 protein of a strain of avian influenza virus. In one embodiment, the strain of avian influenza virus is A/Indonesia/CDC669/2006 (H5N1). The native, full-length H5 protein of this strain is set forth in GenBank Accession No. ABI36428 and is encoded by a nucleic acid having the nucleotide sequence set forth in GenBank Accession No. CY014481. The nucleotide sequence of this nucleic acid is set forth in SEQ ID NO:1. The amino acid sequence of the native, full-length H5 protein of this strain is set forth in SEQ ID NO:2. The native, mature H5 protein (i.e., the H5 protein lacking the signal peptide) of this strain is encoded by a nucleic acid having the nucleotide sequence set forth in SEQ ID NO:3. The amino acid sequence of the native, mature H5 protein is set forth in SEQ ID NO:4. In one embodiment, the modified, mature H5 protein has the modifications S155N, T156A and R189K. These modifications correspond to the modifications at residues 171, 172 and 205, respectively in the full-length H5 protein. The amino acid sequence of the modified, mature H5 protein is set forth in SEQ ID NO:6 which is encoded by a nucleic acid having the nucleotide sequence set forth in SEQ ID NO:5. The amino acid sequence of the modified, full-length H5 protein is set forth in SEQ ID NO:8 which is encoded by a nucleic acid having the nucleotide sequence set forth in SEQ ID NO:7. The modified H5 is also sometimes referred to herein as an epitope-chimeric H5 (EC H5).

In a second aspect, the present invention provides a recombinant avian influenza virus comprising the modified H5 protein described herein. The recombinant avian influenza virus may include the modified H5 protein in the genetic background of an avian influenza virus. The avian influenza virus may be a master strain virus. In one embodiment, the recombinant avian influenza virus may be used as a vaccine. The recombinant avian influenza virus may be included in an immunization kit. In another embodiment, the recombinant avian influenza virus may be used as a diagnostic reference virus in a hemagglutinin inhibition (HI) assay. The recombinant avian influenza virus may be included in a hemagglutinin inhibition (HI) assay kit. In some embodiments, the recombinant avian influenza virus is produced by a reverse genetics process.

Recently developed reverse-genetics systems can be used to manipulate the influenza viral genome (Palese et al., 1996; Neumann and Kawaoka, 1999; Neumann et al., 1999; Fodor et al., 1999; U.S. Patent Application Publication No. 2004/0029251). For example, it has been demonstrated that the plasmid-driven expression of eight influenza vRNAs from a pol I promoter and all mRNAs from a polII promoter result in the formation of infectious influenza A virus (Hoffmann et al 2000; US Patent Application Publication No. 2002/0164770, which is incorporated by reference for its description of a minimal plasmid reverse genetics system, and for its description of genetic engineering methods). These recombinant methods allow for the specific production of influenza virus types with specific alterations to the polypeptide amino acid sequence. A HA molecule containing a desired substitution may be part of a recombinant influenza virus. The recombinant influenza virus may be made by any means known to those of skill in the art, including through a genetic engineering method such as the "plasmid only" system (Hoffmann et al., 2002). The recombinant influenza virus may be derived from a H5N1 virus. The recombinant virus may have the genetic background of a H1N1 virus used in vaccine development such as A/PR/8/34 virus or any influenza A virus, including cold-adapted strains and attenuated strains. The nucleic acid corresponding to the HA molecule sequence may be isolated from the virus and sequenced.

Techniques to isolate and modify specific nucleic acids and proteins are well known to those of skill in the art. In accordance with the present invention there may be employed conventional molecular biology, microbiology, and recombinant DNA techniques within the skill of the art. Such techniques are explained fully in the literature. See, e.g., Green and Sambrook, 2012, *Molecular Cloning*, 4th Ed. (Cold Spring Harbor Laboratory Press, Cold Spring Harbor, N.Y.); Glover, 1985, *DNA Cloning* (IRL Press, Oxford); *Oligonucleotide Synthesis* (M. J. Gait ed. 1984); *Nucleic Acid Hybridization* (B. D. Hames & S. J. Higgins eds. 1984); *Transcription And Translation* (B. D. Hames & S. J. Higgins, eds. (1984)); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); Ausubel et al., 1992, *Current Protocols in Molecular Biology* (John Wiley & Sons, including periodic updates). These techniques include site directed mutagenesis employing oligonucleotides with altered nucleotides for generating PCR products with mutations (e.g., the "Quikchange" kit manufactured by Stratagene).

In a third aspect, the present invention provides a monovalent H5 vaccine for the prevention of a disease in a subject, wherein the disease is associated with an H5N1 subtype of avian influenza virus. In accordance with this aspect, the monovalent H5 vaccine comprises a prophylactically effective amount of an immunogenic agent. In one embodiment, the immunogenic agent comprises a modified H5 protein described herein or antigenic portion thereof or a nucleic acid encoding the modified H5 protein described herein or antigenic portion thereof. In an additional embodiment, the antigenic portion includes an epitope of the modified H5 protein described herein. In a further embodiment, the subjects may be humans, domestic animals (dog, cat, monkey etc.); livestock (horse, cow, sheep, goat, pig etc.), wild birds (wild geese, wild ducks, etc.) and domestic birds (chicken, duck, geese etc.). In one embodiment, the immunogenic agent is virus comprising the modified H5 protein described herein or is a recombinant virus as described herein. In another embodiment, the virus or recombinant virus is inactivated. In an additional embodiment, the virus or recombinant virus is an attenuated virus. In another embodiment, the virus or recombinant virus is in the form of a virosome or a virus-like particle (U.S. Pat. No. 8,592,197). In a further embodiment, the virus or recombinant virus is egg-derived or cell culture-derived. In another embodiment, the immunogenic agent is a split virus comprising the modified H5 protein described herein or a split virus antigenic preparation.

In one embodiment, the immunogenic agent is the modified H5 protein or antigenic portion thereof. In another embodiment, the modified H5 protein or antigenic portion thereof has been isolated. In an additional embodiment, the modified H5 protein or antigenic portion thereof is produced by an expression system. In one embodiment, the expression system is any expression system, such as a viral expression vector in which the modified H5 protein or antigenic portion thereof is presented or displayed on the surface of the virus. In one embodiment, the viral expression vector is any viral expression vector such as a modified vaccinia virus expression vector, an adenovirus expression vector, a poxvirus expression vector, a baculovirus expression vector and the like. In one embodiment, the expression vector is a baculovirus expression vector and the virus presenting or displaying the modified H5 protein or antigenic portion thereof is a baculovirus. In another embodiment, the immunogenic agent is a nucleic acid encoding the modified H5 protein or antigenic portion thereof which is capable of expression in the subject. The production and use of such vectors or expression systems are well known in the art. See, for example, U.S. Pat. No. 8,592,558.

In another embodiment, the immunogenic agent is a virus or recombinant virus comprising the modified H5 protein. The virus or recombinant virus can be an inactivated virus which comprises the modified H5 protein as described herein, an apathogenic version of a live virus comprising the modified H5 protein as described herein, preparation and/or fragments of a virus, wherein said preparation and/or fragment comprise the modified H5 protein as described herein. The production and use of such immunogenic agents are well known in the art. See, for example, U.S. Pat. No. 8,592,558.

Strategies to enhance influenza vaccine effectiveness include the use of adjuvants (Wood and Williams, supra), co-administration of immunostimulatory molecules (Salgaller and Lodge, 1998) and mucosal vaccination strategies. Mucosal immunization strategies include encapsulating the virus in microcapsules (U.S. Pat. Nos. 5,075,109, 5,820,883, and 5,853,763) and using an immunopotentiating membranous carrier (WO 98/0558). In addition, the immunogenicity of orally administered immunogens can be enhanced by using red blood cells (rbc) or rbc ghosts (U.S. Pat. No. 5,643,577), or by using blue tongue antigen (U.S. Pat. No. 5,690,938). See also, U.S. Pat. No. 8,592,558.

If necessary, an immunogenic agent may be formulated into a composition as neutral or salt forms. Pharmaceutically acceptable salts include the acid addition salts (formed with free amino groups of the peptide) and which are formed with inorganic acids such as, for example, hydrochloric or phosphoric acids, or such organic acids such as acetic, oxalic, tartaric, maleic, and the like. Salts formed with the free carboxyl groups may also be derived from inorganic basis such as, for example, sodium, potassium, ammonium, calcium, or ferric hydroxides, and such organic basis as isopropylamine, trimethylamine, 2-ethylamino ethanol, histidine, procaine, and the like.

Formulation of the pharmaceutical composition according to the invention can be accomplished according to standard methodology know to those skilled in the art. In general, suitable compositions may be prepared according to methods which are known to those of ordinary skill in the art and may include pharmaceutically acceptable diluents, adjuvants and/or excipients. The diluents, adjuvants and excipients must be "acceptable" in terms of being compatible with the other ingredients of the composition, and not deleterious to the recipient thereof. See, e.g., Remington: The Science and Practice of Pharmacy, 21st Ed., Ed. D. B. Troy, Lippincott, Williams & Wilkins, Baltimore, 2006, hereby incorporated by reference herein. See also U.S. Pat. No. 8,592,558.

Examples of pharmaceutically acceptable diluents are demineralised or distilled water; saline solution; vegetable based oils such as peanut oil, safflower oil, olive oil, cottonseed oil, maize oil, sesame oils such as peanut oil, safflower oil, olive oil, cottonseed oil, maize oil, sesame oil, arachis oil or coconut oil; silicone oils, including polysiloxanes, such as methyl polysiloxane, phenyl polysiloxane and methylphenyl polysolpoxane; volatile silicones; mineral oils such as liquid paraffin, soft paraffin or squalane; cellulose derivatives such as methyl cellulose, ethyl cellulose, carboxymethylcellulose, sodium carboxymethylcellulose or hydroxypropylmethylcellulose; lower alkanols, for example ethanol or iso-propanol; lower aralkanols; lower polyalkylene glycols or lower alkylene glycols, for example polyethylene glycol, polypropylene glycol, ethylene glycol, propylene glycol, 1,3-butylene glycol or glycerin; fatty acid esters such as isopropyl palmitate, isopropyl myristate or ethyl oleate; polyvinylpyrridone; agar; carrageenan; gum tragacanth or gum acacia, and petroleum jelly. Typically, the carrier or carriers will form from 1% to 99.9% by weight of the compositions. Most preferably, the diluent is saline.

For administration as an injectable solution or suspension, non-toxic parenterally acceptable diluents or carriers can include, Ringer's solution, medium chain triglyceride (MCT), isotonic saline, phosphate buffered saline, ethanol and 1,2 propylene glycol. Some examples of suitable carriers, diluents, excipients and adjuvants for oral use include peanut oil, liquid paraffin, sodium carboxymethylcellulose, methylcellulose, sodium alginate, gum acacia, gum tragacanth, dextrose, sucrose, sorbitol, mannitol, gelatine and lecithin. In addition these oral formulations may contain suitable flavouring and colourings agents. When used in capsule form the capsules may be coated with compounds such as glyceryl monostearate or glyceryl distearate which delay disintegration.

Adjuvants typically include emollients, emulsifiers, thickening agents, preservatives, bactericides and buffering agents. Adjuvants or immunostimulatory components useful in the preparation of the compositions include, and are not limited to, aluminum salts, mineral oils, Mycobacterial products (e.g., Freund's complete or incomplete adjuvants) or vehicles such as a mixture of the plant glycoside saponin, cholesterol and phosphatidylcholine that provides a vehicle for presentation of several copies of the protein on a cage-like structure. For purposes of this specification, an adjuvant is a substance that accentuates, increases, moderates or enhances the immune response to an immunogen or antigen. Adjuvants typically enhance both the humor and cellular immune response but an increased response to either in the absence of the other qualifies to define an adjuvant. Moreover, adjuvants and their uses are well known to immunologists and are typically employed to enhance the immune response when doses of immunogen are limited, when the immunogen is poorly immunogenic, or when the route of administration is sub-optimal. Thus the term "adjuvating amount" is that quantity of adjuvant capable of enhancing the immune response to a given immunogen or antigen. The mass that equals an "adjuvating amount" will vary and is dependant on a variety of factors including, but not limited to, the characteristics of the immunogen, the quantity of immunogen administered, the host species, the route of administration, and the protocol for administering the immunogen. The "adjuvating amount" can readily be quantified by routine experimentation given a particular set of circumstances. This is well within the ordinarily skilled artisan's purview and typically employs the use of routine dose response determinations to varying amounts of administered immunogen and adjuvant. Responses are measured by determining serum antibody titers or cell-mediated responses raised to the immunogen using enzyme linked immunosorbant assays, radio immune assays, hemagglutination assays and the like. The use of adjuvants is well known in the art. See, for example, U.S. Pat. No. 8,592,558.

In one embodiment, the adjuvant is added in an amount of about 100 μg to about 10 mg per dose. In another embodiment, the adjuvant is added in an amount of about 500 μg to about 10 mg per dose. In a further embodiment, the adjuvant is added in an amount of about 500 μg to about 5 mg per dose. In an additional embodiment, the adjuvant is added in an amount of about 750 μg to about 2.5 mg per dose. In another embodiment, the adjuvant is added in an amount of about 1 mg per dose.

Solid forms for oral administration may contain binders acceptable in human and veterinary pharmaceutical practice, sweeteners, disintegrating agents, diluents, flavourings, coating agents, preservatives, lubricants and/or time delay agents. Suitable binders include gum acacia, gelatine, corn starch, gum tragacanth, sodium alginate, carboxymethylcellulose or polyethylene glycol. Suitable sweeteners include sucrose, lactose, glucose, aspartame or saccharine. Suitable disintegrating agents include corn starch, methylcellulose, polyvinylpyrrolidone, guar gum, xanthan gum, bentonite, alginic acid or agar. Suitable diluents include lactose, sorbitol, mannitol, dextrose, kaolin, cellulose, calcium carbonate, calcium silicate or dicalcium phosphate. Suitable flavouring agents include peppermint oil, oil of wintergreen, cherry, orange or raspberry flavouring. Suitable coating agents include polymers or copolymers of acrylic acid and/or methacrylic acid and/or their esters, waxes, fatty alcohols, zein, shellac or gluten. Suitable preservatives include sodium benzoate, vitamin E5 alpha-tocopherol, ascorbic acid, methyl paraben, propyl paraben or sodium bisulphite. Suitable lubricants include magnesium stearate, stearic acid, sodium oleate, sodium chloride or talc.

Liquid forms for oral administration may contain, in addition to the above agents, a liquid carrier. Suitable liquid carriers include water, oils such as olive oil, peanut oil, sesame oil, sunflower oil, safflower oil, arachis oil, coconut oil, liquid paraffin, ethylene glycol, propylene glycol, polyethylene glycol, ethanol, propanol, isopropanol, glycerol, fatty alcohols, triglycerides or mixtures thereof.

Suspensions for oral administration may further comprise dispersing agents and/or suspending agents. Suitable suspending agents include sodium carboxymethylcellulose, methylcellulose, hydroxypropylmethyl-cellulose, poly-vinyl-pyrrolidone, sodium alginate or acetyl alcohol. Suitable dispersing agents include lecithin, polyoxyethylene esters of fatty acids such as stearic acid, polyoxyethylene sorbitol mono- or di-oleate, -stearate or -laurate, polyoxyethylene sorbitan mono- or di-oleate, -stearate or -laurate and the like. Emulsions for oral administration may further comprise one or more emulsifying agents. Suitable emulsifying agents include dispersing agents as exemplified above or natural gums such as guar gum, gum acacia or gum tragacanth.

Methods for preparing parenterally administrable compositions are apparent to those skilled in the art, and are described in more detail in, for example, Remington: *The Science and Practice of Pharmacy,* 21st Ed., Ed. D. B. Troy, Lippincott, Williams & Wilkins, Baltimore, 2006, hereby incorporated by reference herein.

The composition may incorporate any suitable surfactant such as an anionic, cationic or non-ionic surfactant such as sorbitan esters or polyoxyethylene derivatives thereof. Suspending agents such as natural gums, cellulose derivatives or inorganic materials such as silicaceous silicas, and other ingredients such as lanolin, may also be included.

Preparation of the compositions uses routine methods known to persons skilled in the art. Typically, such compositions are prepared as injectables, either as liquid solutions or suspensions; solid forms suitable for solution in, or suspension in, liquid prior to injection may also be prepared. The preparation may also be emulsified. The active immunogenic ingredients are often mixed with excipients that are pharmaceutically acceptable and compatible with the active ingredient.

In a fourth aspect, the present invention provides a method for producing protective immunity to an avian influenza virus which comprises administering to a subject a prophylactically effective amount of a monovalent H5 vaccine described herein.

The compositions, of the present invention may be administered to a subject in the form of a solid, liquid or aerosol at a suitable, pharmaceutically effective dose. Examples of solid compositions include pills, creams, and implantable dosage units. Pills may be administered orally. Therapeutic creams may be administered topically. Implantable dosage units may be administered locally, for example, at a tumor site, or may be implanted for systematic release of the therapeutic composition, for example, subcutaneously. Examples of liquid compositions include formulations adapted for injection intramuscularly, subcutaneously, intravenously, intra-arterially, and formulations for topical and intraocular administration. Examples of aerosol formulations include inhaler formulations for administration to the lungs.

The compositions may be administered by standard routes of administration. The particular route of administration to be used in any given circumstance will depend on a number of factors, including the nature of the disease to be treated, the severity and extent of the disease, the required dosage of the particular compounds to be delivered and the potential side-effects of the desired vaccines or compositions. For example, in circumstances where it is required that appropriate concentrations of the desired vaccines or compositions are delivered directly to the site to be treated, administration may be regional rather than systemic. Regional administration provides the capability of delivering very high local concentrations of the desired vaccines or compositions to the required site and thus is suitable for achieving the desired therapeutic or preventative effect whilst avoiding exposure of other organs of the body to the vaccines or compositions and thereby potentially reducing side effects. Administration strategies are well known in the art. See, for example, U.S. Pat. No. 8,592,558.

In general, the composition may be administered by topical, oral, rectal, nasal, interdermal, intraperitoneal, or parenteral (for example, intravenous, subcutaneous, or intramuscular) routes. In addition, the composition may be incorporated into sustained release matrices such as biodegradable polymers, the polymers being implanted in the vicinity of where delivery is desired, for example, at the site of a tumor. The method includes administration of a single dose, administration of repeated doses at predetermined time intervals, and sustained administration for a predetermined period of time. A sustained release matrix, as used herein, is a matrix made of materials, usually polymers which are degradable by enzymatic or acid/base hydrolysis or by dissolution. Once inserted into the body, the matrix is acted upon by enzymes and body fluids. The sustained release matrix desirably is chosen by biocompatible materials such as liposomes, polylactides (polylactide acid), polyglycolide (polymer of glycolic acid), polylactide co-glycolide (copolymers of lactic acid and glycolic acid), polyanhydrides, poly(ortho)esters, polypeptides, hyaluronic acid, collagen, chondroitin sulfate, carboxylic acids, fatty acids, phospholipids, polysaccharides, nucleic acids, polyamino acids, amino acids such phenylalanine, tyrosine, isoleucine, polynucleotides, polyvinyl propylene, polyvinylpyrrolidone and silicone. A preferred biodegradable matrix is a matrix of one of either polylactide, polyglycolide, or polylactide co-glycolide (co-polymers of lactic acid and glycolic acid).

If desired, devices or compositions containing the immunogenic agents suitable for sustained or intermittent release could be, in effect, implanted in the body or topically applied thereto for the relatively slow release of such materials into the body.

Administration of an expression vector or host cell may include delivery via direct oral intake, systemic injection, or delivery to selected tissue(s) or cells, or indirectly via delivery to cells isolated from a subject or a compatible donor. With regard to nucleic acid based compositions, all modes of delivery of such compositions are contemplated by the present invention.

The compositions may also be administered in the form of liposomes. Liposomes are generally derived from phospholipids or other lipid substances, and are formed by mono- or multi-lamellar hydrated liquid crystals that are dispersed in an aqueous medium. Any non-toxic, physiologically acceptable and metabolisable lipid capable of forming liposomes can be used. The compositions in liposome form may contain stabilisers, preservatives, excipients and the like. The preferred lipids are the phospholipids and the phosphatidyl cholines (lecithins), both natural and synthetic. Methods to form liposomes are well known in the art.

The effective dose level of the administered compound for any particular subject will depend upon a variety of factors including: the type of disease being treated and the stage of the disease; the activity of the compound employed; the composition employed; the age, body weight, general health, sex and diet of the subject; the time of administration; the route of administration; the rate of sequestration of compounds; the duration of the treatment; drugs used in combination or coincidental with the treatment, together with other related factors well known in the art.

Proteinaceous pharmaceutically active matter may be present in amounts between 1 ng and 10 mg per dose. Generally, the regime of administration should be in the range of between 0.1 µg and 10 mg of the antibody according to the invention, particularly in a range 1.0 µg to 1.0 mg, and more particularly in a range of between 1.0 µg and 100 µg, with all individual numbers falling within these ranges also being part of the invention. If the administration occurs through continuous infusion a more proper dosage may be in the range of between 0.01 µg and 10 mg units per kilogram of body weight per hour with all individual numbers falling within these ranges also being part of the invention.

Administration will generally be parenterally, e.g., intravenously. Preparations for parenteral administration include sterile aqueous or non-aqueous solutions, suspensions and emulsions. Non-aqueous solvents include without being limited to it, propylene glycol, polyethylene glycol, vegetable oil such as olive oil, and injectable organic esters such as ethyl oleate. Aqueous solvents may be chosen from the group consisting of water, alcohol/aqueous solutions, emulsions or suspensions including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose) and others. Preservatives may also be present such as, for example, antimicrobials, antioxidants, chelating agents, inert gases, etc.

The pharmaceutical composition may further comprise proteinaceous carriers such as, for example, serum albumin or immunoglobulin, particularly of human origin. Further biologically active agents may be present in the pharmaceutical composition of the invention dependent on the intended use.

In a fifth aspect, the present invention provides a method for the prevention or treatment of a disease associated with an avian influenza virus which comprises administering to a subject a prophylactically effective amount of a monovalent H5 vaccine. In one embodiment, the prevention or treatment delays the onset of or slows the rate of progression of avian influenza. The monovalent H5 vaccine is as described above. Suitable compositions, administration and dosages are as described above.

In a sixth aspect, the present invention provides use of a monovalent H5 vaccine for stimulating an immune response to an avian influenza virus. The monovalent H5 vaccine is as described above.

In a seventh aspect, the present invention provides a use of the modified H5 protein described herein or the recombinant avian influenza virus described herein for the manufacture of a medicament for eliciting a protective immune response in a subject.

In an eighth aspect, the present invention provides a use of the modified H5 protein described herein or the recombinant avian influenza virus described herein for the manufacture of a medicament for preventing a subject from becoming afflicted with H5N1 subtype avian influenza.

In a ninth aspect, the present invention provides a use of the modified H5 protein described herein or the recombinant avian influenza virus described herein for the manufacture of a medicament for delaying the onset of or slowing the rate of H5N1 subtype avian influenza in an H5N1 avian influenza-infected subject.

In a tenth aspect, the present invention provides a method of making a vaccine comprising using the modified H5 protein described herein or the recombinant avian influenza virus described herein.

In an eleventh aspect, the present invention provides a use of the modified H5 protein described herein or of the recombinant avian influenza virus described herein for vaccine development.

In a twelfth aspect, the present invention provides a modified H5 protein described herein or a recombinant avian influenza virus described herein for use in vaccine development As shown herein, a broadly immunogenic H5 was developed based on epitope engineering in order to present representative epitopes from different major H5N1 strains. The use of a monovalent vaccine expressing the epitope-chimeric H5 against multiple clades of H5N1 s was shown in a mouse model challenged with phylogenetically variant H5N1 strains.

The practice of the present invention employs, unless otherwise indicated, conventional techniques of chemistry, molecular biology, microbiology, recombinant DNA, genetics, immunology, cell biology, cell culture and transgenic biology, which are within the skill of the art. See, e.g., Maniatis et al., 1982, *Molecular Cloning* (Cold Spring Harbor Laboratory Press, Cold Spring Harbor, N.Y.); Sambrook et al., 1989, *Molecular Cloning*, 2nd Ed. (Cold Spring Harbor Laboratory Press, Cold Spring Harbor, N.Y.); Sambrook and Russell, 2001, *Molecular Cloning*, 3rd Ed. (Cold Spring Harbor Laboratory Press, Cold Spring Harbor, N.Y.); Green and Sambrook, 2012, *Molecular Cloning*, 4th Ed. (Cold Spring Harbor Laboratory Press, Cold Spring Harbor, N.Y.); Ausubel et al., 1992, *Current Protocols in Molecular Biology* (John Wiley & Sons, including periodic updates); Glover, 1985, *DNA Cloning* (IRL Press, Oxford); Russell, 1984, *Molecular biology of plants: a laboratory course manual* (Cold Spring Harbor Laboratory Press, Cold Spring Harbor, N.Y.); Anand, *Techniques for the Analysis of Complex Genomes*, (Academic Press, New York, 1992); Guthrie and Fink, *Guide to Yeast Genetics and Molecular Biology* (Academic Press, New York, 1991); Harlow and Lane, 1988, *Antibodies*, (Cold Spring Harbor Laboratory Press, Cold Spring Harbor, N.Y.); *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Methods In Enzymology*, Vols. 154 and 155 (Wu et al. eds.), *Immunochemical Methods In Cell And Molecular Biology* (Mayer and Walker, eds., Academic Press, London, 1987); *Handbook Of Experimental Immunology*, Volumes I-IV (D. M. Weir and C. C. Blackwell, eds., 1986); Riott, *Essential Immunology*, 6th Edition, Blackwell Scientific Publications; Oxford, 1988; Fire et al., *RNA Interference Technology: From Basic Science to Drug Development*, Cambridge University Press, Cambridge, 2005; Schepers, *RNA Interference in Practice*, Wiley-VCH, 2005; Engelke, *RNA Interference (RNAi): The Nuts & Bolts of siRNA Technology*, DNA Press, 2003; Gott, *RNA Interference, Editing, and Modification: Methods and Protocols (Methods in Molecular Biology)*, Human Press, Totowa, N.J., 2004; Sohail, *Gene Silencing by RNA Interference: Technology and Application*, CRC, 2004.

EXAMPLES

The present invention is described by reference to the following Examples, which is offered by way of illustration and is not intended to limit the invention in any manner. Standard techniques well known in the art or the techniques specifically described below were utilized.

Example 1

Materials and Methods

Ethics Statement:

All animal experiments were carried out in accordance with the Guidelines for Animal Experiments of the National Institute of Infectious Diseases (NIID). Experimental protocols were reviewed and approved by Institutional Animal Care and Use Committee of the Temasek Life Sciences Laboratory, National University of Singapore, Singapore. (IACUC approval number TLL-12-014).

All experiments involving human H5N1 strains were performed in a biosafety level 3 (BSL-3) containment laboratory in compliance with CDC/NIH and WHO recommendations and were approved by the Agri Veterinary Authority (AVA) of Singapore.

Viruses and Cell Lines:

H5N1 human influenza viruses A/Indonesia/CDC669/2006 was obtained from the Ministry of Health (MOH), Republic of Indonesia. The H5N1 viruses from different phylogenetic clades or subclades were rescued by reverse genetics. Briefly, the hemagglutinin (HA) and neuraminidase (NA) genes of H5N1 viruses from clades 1.0 (A/Vietnam1203/04), clade 2.2.1.1 (A/Egypt/3300-NAMRU3/2008), clade 2.2(A/barheaded goose/Qinghai/12/05), 2.3.2.1 (A/Akita/1/08), 2.3 (A/Anhui/1/05 and A/Jiangsu/2/07), 4 (A/goose/Guiyang/337/06), 7.0 (A/chicken/Shanxi/2/06) and 7.1 (A/Vietnam/NCVD-03/08) were synthesized (GenScript) based on the sequences in the NCBI influenza virus database. The synthetic HA and NA genes were cloned into a dual promoter plasmid for influenza A virus reverse genetics (Prabakaran et al., 2009a). The dual-promoter plasmids were obtained from the Centers for Disease Control and Prevention, Atlanta, Ga. Reassortant viruses were rescued by transfecting plasmids containing HA and NA along with the remaining six influenza virus genes derived from high-growth master strain A/Puerto Rico/8/34 (H1N1) into cocultured 293T and MDCK cells by using Lipofectamine 2000 (Invitrogen Corp.). At 72 h posttransfection the culture medium was inoculated into embryonated eggs or MDCK cells. The HA and NA genes of reassortant viruses from the second passage were sequenced to confirm the presence of the introduced HA and NA genes and the absence of mutations. Stock viruses were propagated in the allantoic cavity of 10-day-old embryonated eggs, and virus containing allantoic fluid was harvested and stored in aliquots at 80° C. Virus content was determined by a standard hemagglutination assay as described previously (He et al., 2008).

MDCK cells were maintained in Dulbeccos Modified Eagle Medium (DMEM; Life Technologies, USA) containing 10% Fetal Bovine Serum (FBS; Life Technologies, USA). 293T were maintained in Opti-MEMI (Life Technologies, USA) containing 5% FBS. After 48 h the transfected supernatants were collected and virus titers were determined by standard hemagglutination assays. The tissue culture infectious dose 50 ($TCID_{50}$) of reassortant virus was then calculated by the Muench-Reed method (Reed and Muench, 1938).

Production and Characterization of mAb:

A panel of different H5 neutralizing mAbs was used. The mAbs were produced as described previously. Briefly, BALB/c mice were immunized twice 2 weeks apart by the subcutaneous injection of individual BEI-inactivated H5N1 virus (A/Indonesia/CDC669/2006 A/Vietnam/1203/2004 or A/Anhui/1/05) mixed with Montanide ISA563 adjuvant (Seppic, France). Mice received an additional intravenous injection of the same viral antigen 3 days before the fusion of splenocytes with SP2/0 cells. Hybridoma culture supernatants were screened by immunofluorescence assays. Hybridomas that produced specific mAbs were cloned by limiting dilution, expanded, and further subcultured. The hybridoma culture supernatant was clarified and tested for the hemagglutination inhibition activity as described below.

Hemagglutination Inhibition Assay:

Hemagglutination inhibition (HI) assays were performed as described previously (Prabhu et al., 2009). Briefly, mAbs or receptor-destroying enzyme (RDE)-treated sera were serially diluted (2 fold) in V-bottom 96-well plates and mixed with 4 HA units of H5 virus. Plates were incubated for 30 min at room temperature, and 1% chicken RBCs were added to each well. The hemagglutination inhibition endpoint was the highest antibody dilution in which agglutination was not observed.

Microneutralization Assay:

Neutralization activity of mAb or serum against H5 strains was analyzed by microneutralization assay as previously described (He et al., 2013). Briefly, antibody samples were serially two-fold diluted and incubated with 100 TCID50 of different clades of H5 strains for 1 h at room temperature and plated in duplicate onto MDCK cells grown in a 96-well plate. The neutralizing titer was assessed as the highest antibody dilution in which no cytopathic effect was observed by light microscopy.

Immunization and Challenge:

Specific-pathogen-free female BALB/c mice (6 weeks old) were obtained from the Laboratory Animals Centre, National University of Singapore. 10 mice per each experimental group were vaccinated subcutaneously two times at a regular interval of 14 days with 100 ul (HA titer, 128) of inactivated RG H5N1 virus carrying the universal HA or other inactivated H5N1 viruses (A/Indonesia/CDC669/2006 and A/Vietnam/1203/2004), with the adjuvant Montanide ISA563 (water-in-oil emulsion; Seppic, France). PBS with the same adjuvant was used as a reference vaccine control. The serum was collected from 10 mice per experimental group on day 28. Levels of hemagglutination inhibition activity and serum cross-clade neutralizing antibody were measured.

Three weeks after the final vaccination, mice were transferred into an animal BSL-3 containment facility. 8 mice per group were challenged intranasally with 5 50% mouse lethal doses (MLD50) of clade 1.0 (A/Vietnam/1203/2004), clade 2.1 (A/Indonesia/CDC669/06), clade 2.3 (A/Anhui/1/05) and clade 2.2.1.1 (A/Egypt/3300-NAMRU3/2008) HPAI H5N1 virus strains. The MLD50 of influenza virus required for intranasal challenge experiments was predetermined. Mice were observed daily to monitor body weight and mortality. Monitoring continued until all animals died or until day 14 after challenge.

Histopathological Analysis:

Mice were necropsied, and the lungs were stored in 10% (wt/vol) neutral buffered formalin, embedded in paraffin, and sectioned. The sections were deparaffinized using Histchoice (Amersco) and rehydrated in sequentially graduated ethanol baths. The slides were stained with hematoxylin and eosin and pathological evaluation was performed by light microscope (Olympus, UK). The images were captured by digital imaging system (Nikon, USA).

Statistical Analysis:

The data are expressed as arithmetic means±standard deviations (SD) or standard errors (SE). An unpaired two-tailed Student's t test was performed to determine the level of significance in the difference between the means of two groups. One-way analysis of variance (ANOVA) was also used to test for differences between groups, and the Tukey honestly significant difference (HSD) post hoc test was used to determine which groups were significantly different from the rest. All statistical analyses were done with SigmaStat 2.0 (Jandel Corporation) software. The level of significance was expressed as a P value of 0.05.

Example 2

Combination of Major H5 Epitopes from Different Clades on One Single H5

Isolated from a human lethal case in 2006, A/Indonesia/CDC669/06 was one of the representative strains from the clade 2, the largest clade in H5 phylogenetic trees (Shore et al., 2013). In this study, H5 of CDC669 was selected as the backbone for the epitope chimeric H5 (EC H5). The protein sequences of the major antigenic sites equivalent to those in H1 structure (Caton et al., 1982) were aligned among H5N1s from different clades (FIG. 1). Amino acid positions 155, 156 and 189 were indicated to be some of the most variable sites in all the antigenic regions on H5. The three amino acids were mutated to other predominant forms on the sites of other clades, which are different from the original ones on the wild type CDC669. The three mutations were indicated as S155N, T156A and R189K individually. The rest of amino acids involved in epitopes remained unchanged to sustain the antigenic features of clade 2.1 CDC669. Hence, the representative epitopes of different clades were displayed together on a single H5 in order to elicit cross-clade immunity.

Example 3

Characterization of the Epitope-Chimeric H5

The epitope-chimeric H5 was expressed in a RG H5N1 virus with PR8 background. Expression of H5 was determined with mAb 2D9, a mAb with broad recognition of H5 (Prabakaran et al., 2009b), in infected MDCK cells. Hemagglutination activity was detected in HA test with the EC H5. A panel of neutralizing mAbs was produced previously in mice immunized with clade 1.0 (A/Vietnam/1203/2004), clade 2.1 (A/Indonesia/CDC669/06) or clade 2.3 (A/Anhui/1/05) individually. HI tests with these mAbs were performed to compare the antigenicity between EC H5 and wild type CDC669. As shown in Table 1, the EC H5 can be recognized and neutralized by all the H5 mAbs tested, except 11G12, a mAb specific to clade 1 (He and Kwang, 2013). CDC669 fails to react with many mAbs which were generated from other H5N1s. Some mAbs which are able to neutralize CDC669 showed a higher titer against the EC H5 in HI test. The observations indicate that the EC H5 presents different antigenic properties from CDC669. The mutations in the epitopes allow the EC H5 to be susceptible to neutralization with variant monoclonal antibodies.

Example 4

Cross-Clade Neutralizing Antibody Titers in Sera

Figure 2:
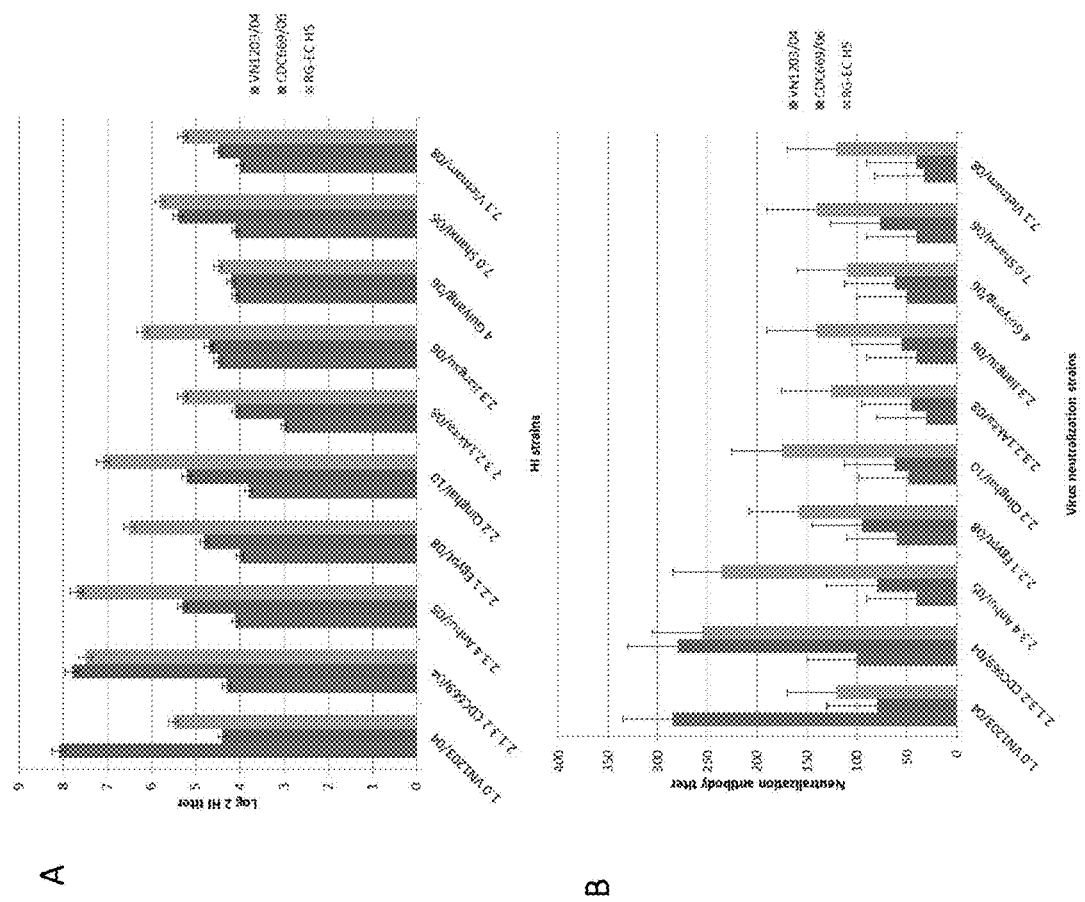
FIGS. 2A and 2B show cross-clade tests with immunized mouse sera. Serum samples were collected on Day 28 (14 days after the final immunization) from mice immunized with RG-EC H5, A/Vietnam/1203/2004, A/Indonesia/CDC669/2006 or PBS respectively.

Hemagglutination inhibition (HI) titers measure the efficacy of the antibody response to inhibit HA function. As shown in FIG. 2A, the sera from mice immunized with RG-EC monovalent vaccine had efficiently induced HAI titer against heterologous viruses of different clades on day 28. Higher titers were observed with sera from the RG-EC group against all the tested strains of clade 1, clade 2, clade 4 and clade 7 as compared to sera from other heterologous monovalent strains. HI titers of samples from RG-EC H5 vaccinated mice were lower than the groups with homologous vaccinations against either clade 1.0 (A/Vietnam/1203/2004) or clade 2.1 (A/Indonesia/CDC669/06). Virus neutralization was performed to determined functional antibodies responsible for the protective immunity against influenza (FIG. 2B). The similar comparison results were observed in both HI and virus neutralization test, confirming that the epitope-chimeric H5 exhibits improved cross-clade immunogenicity and suggesting that EC H5 is able to elicit broader protection against multiple clades of H5N1 than other monovalent strains.

Example 5

Challenge Studies after Vaccination

Figure 3:
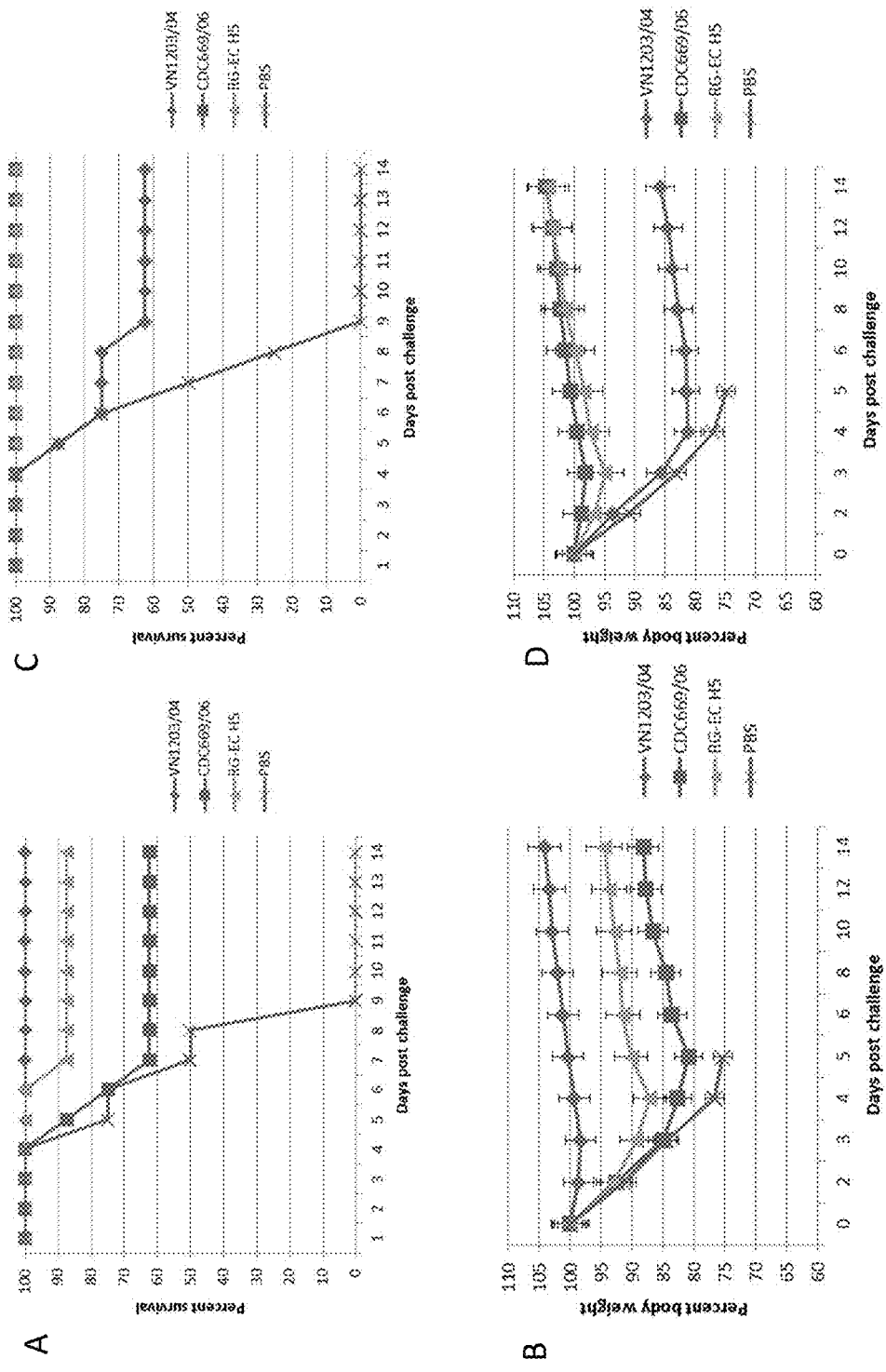
FIGS. 3A-3H show protection of mice against lethal challenge with clade 1.0, clade 2.1, clade 2.2 or clade 2.3 H5N1 virus. The results are expressed in terms of percent survival (FIGS. 3A, 3C, 3E and 3G) and percent body weight (FIGS. 3B, 3D, 3F and 3H) (at the beginning of the trial), respectively. Groups of mice (n=8) were subcutaneously immunized with RG-EC 115, A/Vietnam/1203/2004, A/Indonesia/CDC669/2006 or PBS respectively. Three weeks after the final vaccination, mice were intranasally infected with 5 MLD50 of clade 1.0 (A/Vietnam/1203/2004) (FIGS. 3A, 3B), clade 2.1 A/Indonesia/CDC669/2006 (FIGS. 3C, 3D), clade 2.3.4 A/Anhui/1/05 (FIGS. 3E, 3F) or clade 2.2.1.1 AJEgypt/3300-NAMRU3/2008 (FIGS. 3G, 3hH) HPAI H5N1 virus strains. Mice were monitored throughout a 14-day observation period.
Figure 3:
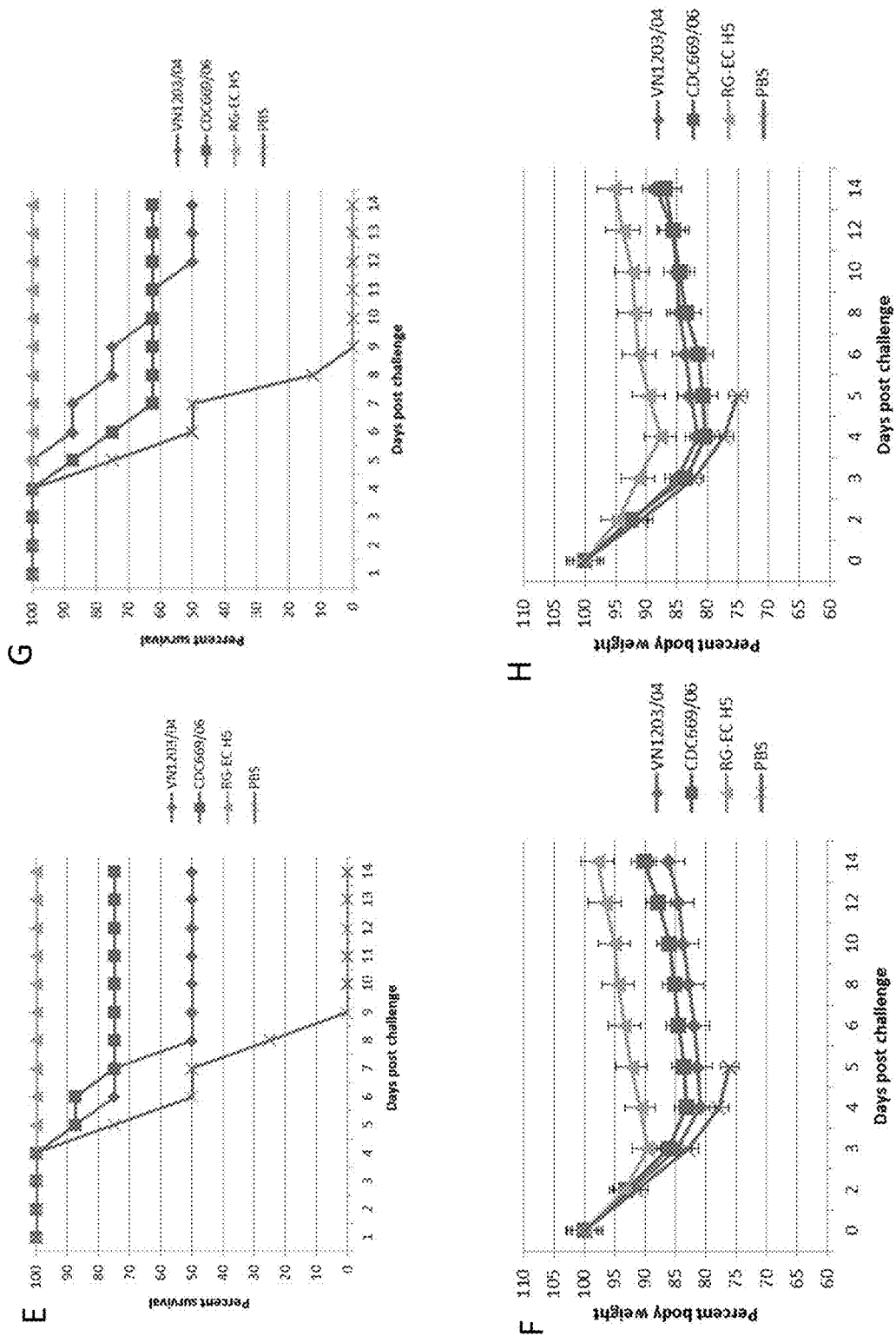

Three weeks after the final immunization, all groups of mice were challenged intranasally with 5 MLD50 of HPAI H5N1 virus strains from clade 1.0 (A/Nietnam/1203/2004), clade 2.1 (A/Indonesia/CDC669/06), clade 2.3 (A/Anhui/1/05) and clade 2.2.1.1 (A/Egypt/3300-NAMRU3/2008). Groups of mice immunized with RG-EC H5 obtained 100% protection against clade 2.1, clade 2.2 and clade 2.3 viruses (FIGS. 3C, 3E and 3G) and 87.5% survival rate against clade 1.0 (FIG. 3A). However, mice immunized with other monovalent H5N1 vaccines showed only 50% to 75% survival rate against any heterologous challenge respectively.

The progression of infection was indicated by various trends of a decrease in body weight for the different groups. In groups of mice immunized with a RG-EC H5 strain, no significant decreases in body weight (≤13.3%) were observed for mice upon the challenges from different heterologous H5N1s respectively (FIGS. 3B, 3D, 3F and 3G)). However, mice vaccinated with other single H5N1 strains showed at least a 17% loss in body weight against any heterologous challenge, although the body weight was gradually regained after 6 days post-challenge. The group of RG-EC H5 presented similar body weight loss (<5.1%) as the group of CDC669 (<1.9%) upon the homologous challenge of CDC669, while showed significant improvements as compared to CDC669 vaccination in preventing weight loss upon other heterologous challenges.

Figure 4:
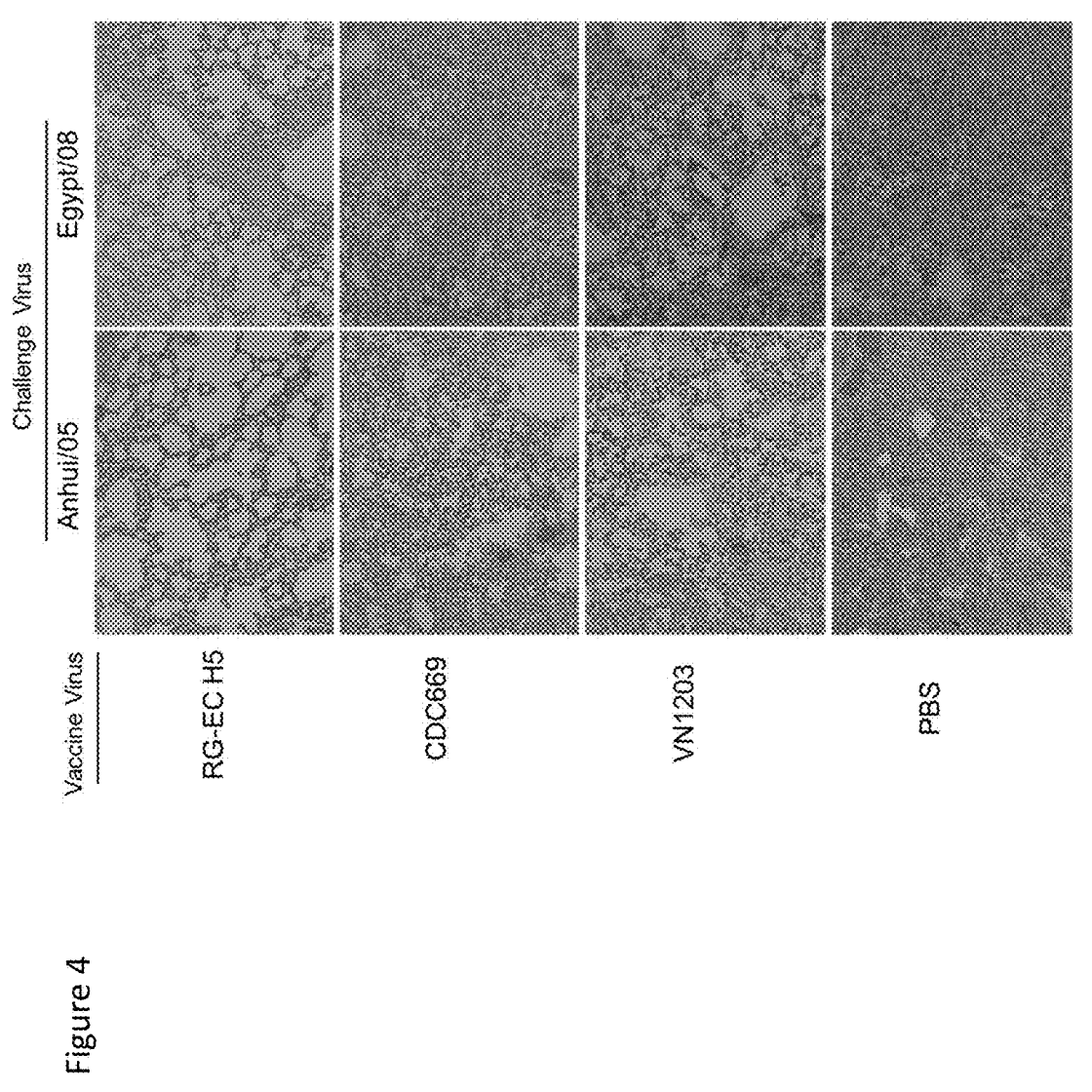

Histopathology studies were performed for the mice vaccinated with different monovalent H5N1 strains and challenged with clade 2.3 (A/Anhui/1/05) or clade 2.2.1.1 (A/Egypt/3300-NAMRU3/2008) HPAI H5N1 viruses. On day 5 postinfection, lungs of mice vaccinated with clade 1.0 (A/Vietnam/1203/2004), clade 2.1 (A/Indonesia/CDC669/06) or PBS, had pulmonary lesions consisting of moderate to severe necrotizing bronchitis and histiocytic alveolitis with associated pulmonary edema upon heterologous challenge (FIG. 4). The mice immunized RG-EC H5 lacked lesions in the lungs upon the challenge from clade 2.3 (A/Anhui/1/05) and had only minimal bronchitis against clade 2.2.1.1 (A/Egypt/3300-NAMRU3/2008) H5N1 viral challenges.

Figure 5:
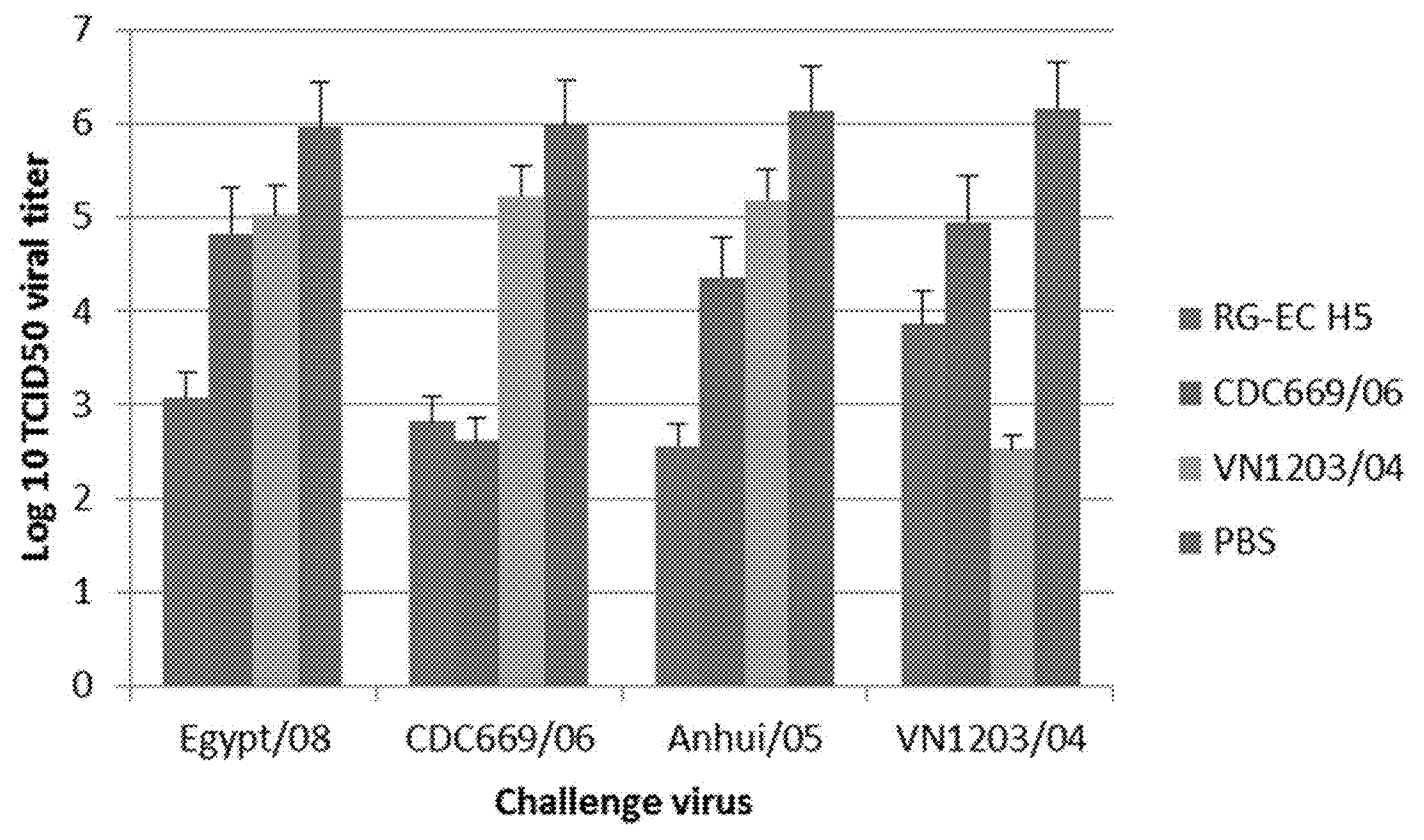

Moreover, virus load in lungs was evaluated in H5 vaccinated mice upon viral challenges by measuring the viral titers in the mouse lungs (FIG. 5). The lungs were collected on day 4 after viral challenge when the high virus titers of more than $10^6$ were detected in the infected but untreated mice which died within the following day. The mice immunized with RG-EC H5 showed lowest viral load upon challenge with clade 2.3 (A/Anhui/1/05) or clade 2.2.1.1 (A/Egypt/3300-NAMRU3/2008) as compared to other monovalent vaccinations. Virus titers in lungs from RG-EC H5 vaccinated mice were at least 10 times lower than the group immunized with clade 2.1 (A/Indonesia/CDC669/06) upon the challenge with clade 1.0 (A/Vietnam/1203/2004), though the group vaccinated with homologous strain presented even lower titers.

All these results indicated that immunization with RG-EC H5 provided more efficacious protection as compared to other monovalent vaccines against variant heterologous challenge.

Example 6

Discussion

The rapid evolution of new sublineages of influenza A/H5N1 virus is considered to be the most likely culprit for the next pandemic (Watanbe et al., 2011). Newer vaccine approaches for pandemic preparedness against these viruses are needed, given the limitations of vaccines currently approved for H5N1 viruses in terms of their production timelines and the ability to induce cross-clade protective immune responses (Prieto-Lara and Llanos-Mendez, 2010). An epitope-chimeric H5 presented in this study meets both needs as a monovalent broad vaccine against variable circulating H5N1s. Having broad reactivity to multiple monoclonal antibodies and anti-sera against different H5N1 clades, the developed single H5N1 elicited effective cross-clade protection against lethal H5N1 challenges in mice.

Considerable amino acid variations within antigenic sites of HA lead to the emergence of antigenically distinct influenza H5N1 viruses (Plotkin et al., 2002). The continuous evolution of H5N1 within each clade has generated multiple second, third and fourth order clades defined by their phylogenetic clustering and genetic distance, especially in clade 2 (Shore et al., 2013; Sun et al., 2013; Younan et al., 2013). Currently, the majority of viruses circulating worldwide and causing human infections were identified in clades 1 and 2, such as clades 1.1, 2.1.3.2, 2.2.1 and 2.3.4 (Forrest et al., 2009; Yang et al., 2009). Therefore, different vaccine combinations from these clades were selected by different research groups and regulatory agencies in order to produce a universal H5N1 vaccine. Recently, clade 2.2.1 A/Egypt/N03072/2010, clade 2.3.2.1 A/Hubei/1/2010 and clade 2.3.4 A/Anhui/1/2005 were selected by the WHO as vaccine candidates based on their history related to human fatal cases. In the previous study in the lab, a vaccine formulation containing H5s of clade 1.0 A/Vietnam/1203/2004, clade 2.1.3.2 A/Indonesia/CDC669/2006 and clade 2.3.4 A/Anhui/1/2005 was confirmed to be effective against multiple clades of H5N1s (Prabakaran et al., 2010). Considering all these recommendations, in order to generate a monovalent H5 which is able to elicit cross protection against all these major H5N1s responsible to human infection, a H5 from a representative circulating strain of clade 2 is preferred. Many H5 mAbs were produced in the lab with different H5N1 antigens. It was noticed that more H5 mAbs with broad spectrum to all clades of H5N1 were generated from CDC669 than any other H5N1 strains (H Je et al., 2010; Ho et al., 2009; Prabakaran et al., 2009a; Prabakaran et al., 2009b), suggesting the cross-clade immunogenicity of CDC 669. Taken together, in the study, A/Indonesia/CDC669/2006 of clade 2.1.3.2 was selected as the backbone for the monovalent universal 115. As shown in the results, after further mutations in the epitopes, the EC H5 from CDC669 gained reactivity to those previously un-reactive mAbs and sustained the original reactivity to CDC669 mAbs. This finding paves way for the application this single EC H5 to a potential universal H5N1 vaccine.

Among all the amino acid variations in antigenic sites; three significant ones were found in Sa (155,156aa), Sb (189aa) and Ca (138-141) sites (Kaverin et al., 2002). Three amino acids in Sa and Sb were mutated to other predominant forms in order to generate the epitope-chimeric H5. The variable region in Ca was kept to be same to wild type CDC669, contributing to the antigenic features of clade 2.1. As a part of receptor binding site, amino acids in the 130 loop is highly variable among different clades (Hensley et al., 2009; Stevens et al., 2006). For example, there are more than 7 amino acid options identified on the 140th aa. Together with other variations in the neighboring positions, the number of possible combinations of amino acids in the 130 loop is very high. A screening may be required to determine the most suitable form for a universal H5 vaccine.

Therefore, the region was unchanged in this study. In the future work, mutations could be induced to this site to improve and expand the immunogenic spectrum of the EC H5 vaccine.

EC-H5 fails to react to mAb 11G12 (He and Kwang, 2013), a monoclonal antibody specific to H5N1 of clade 1, implying the relatively weaker immunogenicity to clade 1. With the mutation on the 189th aa to the same form of the clade 1.0, 87.5%, of mice survived with the RG-EC H5 immunization upon the challenge with VN1203 of clade 1.0. Though 100% protection was not achieved, the performance of RG-EC H5 was much better as compared to wild type CDC669 with a survival rate at 50% against VN1203. This could be further improved by the induction of other mutations in Sa region, such as 152aa, the epitope targeted by mAb 11G12. Tests with various monoclonal antibodies targeting different epitopes can serve as a rapid method to predict the antigenicity of H5s before animal tests and also provide clues for improvement.

Antigenic differences in epitopes may render current vaccines unqualified for the prevention of influenza globally (Fouchier and Smith, 2010). Exploit of multivalent vaccines significantly increases vaccine cost and delays the vaccine developing progress against a sudden influenza outbreak. The availability of a simple and broadly protective vaccine for influenza H5N1 is a high priority in preparedness for a future influenza pandemic. The study provides not only a monovalent vaccine candidate with broad spectrum but also contributes a new method to flu vaccine development. Instead of using the strains from major outbreaks or severe cases, epitope engineering on a single HA to produce an epitope chimeric H5 avoids difficulties in virus strain adaption and multiple antigen co-expression. A monovalent H5 vaccine with broad spectrum to H5N1s worldwide will greatly reduce cost in both vaccine development and production. New combinations of epitopes in a single HA could be easily designed and tested to prevent infection mediated by newly emerged H5N1.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

It will be appreciated that the methods and compositions of the instant invention can be incorporated in the form of a variety of embodiments, only a few of which are disclosed herein. Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

BIBLIOGRAPHY

Aubin, J. T. et al. (2005). Evolution of H5N1 avian influenza viruses in Asia. Emerg Infect Dis 11:1515-21.

Baz, M. et al. (2013). H5N1 vaccines in humans. Virus Res 178:78-98.

Caton, A. J. et al. (1982). The antigenic structure of the influenza virus A/PR/8/34 hemagglutinin (H1 subtype). Cell 31:417-27.

Chen, G. L., and Subbarao, K. (2009). Attacking the flu: neutralizing antibodies may lead to 'universal' vaccine. Nat Med 15:1251-2.

Fodor, E. et al. (1999). Rescue of influenza A virus from recombinant DNA. J Virol 73:9679-82.

Forrest, H. L. et al. (2009). Single- and multiple-clade influenza A H5N1 vaccines induce cross protection in ferrets. Vaccine 27:4187-95.

Fouchier, R. A., and Smith, D. J. (2010). Use of antigenic cartography in vaccine seed strain selection. Avian Dis 54:220-3.

Gambotto, A. et al. (2008). Human infection with highly pathogenic H5N1 influenza virus. Lancet 371:1464-75.

Guan, Y. et al. (2004). H5N1 influenza: a protean pandemic threat. Proc Natl Acad Sci USA 101:8156-61.

He, F., and Kwang, J. (2013). Monoclonal Antibody Targeting Neutralizing Epitope on H5N1 Influenza Virus of Clade 1 and 0 for Specific H5 Quantification. Influenza Res Treat 2013:360675.

He, F. et al. (2008). WSSV ie1 promoter is more efficient than CMV promoter to express H5 hemagglutinin from influenza virus in baculovirus as a chicken vaccine. BMC Microbiol 8:238.

He, F. et al. (2010). Complementary monoclonal antibody-based dot ELISA for universal detection of H5 avian influenza virus. BMC Microbiol 10:330.

Hensley, S. E. et al. (2009). Hemagglutinin receptor binding avidity drives influenza A virus antigenic drift. Science 326:734-6.

Ho, H. T. et al. (2009). Rapid detection of H5N1 subtype influenza viruses by antigen capture enzyme-linked immunosorbent assay using H5- and N1-specific monoclonal antibodies. Clin Vaccine Immunol 16:726-32.

Hoffmann, E. et al. (2000). A DNA transfection system for generation of influenza A virus from eight plasmids. Proc Natl Acad Sci USA 97:6108-13.

Hoffmann, E. et al. (2002). Eight-plasmid system for rapid generation of influenza virus vaccines. Vaccine 20:3165-70.

Hood, L. E. et al. (1984). Immunology, Second Ed., Menlo Park, Calif., Benjamin/Cummings, p. 384.

http colon slash slash www dot who dot int/influenza/
human_animal_interface/
EN_GIP_20131008CumulativeNumberH5N1 cases .pdf
2013

Imai, M. et al. (2012). Experimental adaptation of an influenza H5 HA confers respiratory droplet transmission to a reassortant H5 HA/H1N1 virus in ferrets. Nature 486: 420-8.

Kaverin, N. V. et al. (2002). Structure of antigenic sites on the haemagglutinin molecule of H5 avian influenza virus and phenotypic variation of escape mutants. J Gen Virol 83:2497-505.

Neumann, G. and Kawaoka, Y. (1999). Genetic engineering of influenza and other negative-strand RNA viruses containing segmented genomes. Adv Virus Res 53:265-300.

Neumann, G. et al. (1999). Generation of influenza A viruses entirely from cloned cDNAs. Proc Natl Acad Sci USA 96:9345-50.

Palese, P. et al. (1996). Negative-strand RNA viruses: genetic engineering and applications. Proc Natl Acad Sci USA 93:11354-8.

Peiris, J. S. et al. (2007). Avian influenza virus (H5N1): a threat to human health. Clin Microbiol Rev 20:243-67.

Plotkin, J. B. et al. (2002). Hemagglutinin sequence clusters and the antigenic evolution of influenza A virus. Proc Natl Acad Sci USA 99:6263-8.

Prabakaran, M. et al. (2009a). Development of epitope-blocking ELISA for universal detection of antibodies to human H5N1 influenza viruses. PLoS One 4:e4566.

Prabakaran, M. et al. (2009b). Combination therapy using chimeric monoclonal antibodies protects mice from lethal H5N1 infection and prevents formation of escape mutants. PLoS One 4:e5672.

Prabakaran, M. et al. (2010). Neutralizing epitopes of influenza virus hemagglutinin: target for the development of a universal vaccine against H5N1 lineages. J Virol 84:11822-30.

Prabhu, N. et al. (2009). Prophylactic and therapeutic efficacy of a chimeric monoclonal antibody specific for H5 haemagglutinin against lethal H5N1 influenza. Antivir Ther 14:911-21.

Prieto-Lara, E. and Llanos-Mendez, A. (2010). Safety and immunogenicity of prepandemic H5N1 influenza vaccines: a systematic review of the literature. Vaccine 28:4328-34.

Reed, L. J. and Muench, H. (1938). A simple method of estimating fifty percent endpoints. Am J Hygiene 27:493-497.

Salgaller, M. L. and Lodge, P. A. (1998). Use of cellular and cytokine adjuvants in the immunotherapy of cancer. J Surg Oncol 68:122-38.

Shore, D. A. et al. (2013). Structural and Antigenic Variation among Diverse Clade 2 H5N1 Viruses. PLoS One 8:e75209.

Stevens, J. et al. (2006). Structure and receptor specificity of the hemagglutinin from an H5N1 influenza virus. Science 312:404-10.

Sun, H. et al. (2013). Comparative virus replication and host innate response in human cells infected with 3 prevalent clades (2.3.4, 2.3.2 and 7) of highly pathogenic avian influenza H5N1 viruses. J Virol, $JVI$.02510-13; published ahead of print 16 Oct. 2013.

Watanabe, Y. et al. (2011). Acquisition of human-type receptor binding specificity by new H5N1 influenza virus sublineages during their emergence in birds in Egypt. PLoS Pathog 7:e1002068.

WHO et al. (2008). Toward a unified nomenclature system for highly pathogenic avian influenza virus (H5N1). Emerg Infect Dis 14:e1.

Wu, F. et al. (2007). Characterization of immunity induced by M2e of influenza virus. Vaccine 25:8868-73.

Yang, J. X. et al. (2009). [Type and subtype distribution of influenza virus and genetic evolution of hemagglutinin in Shanghai area in duration of 2004-2008]. Zhonghua Yu Fang Yi Xue Za Zhi 43:305-8.

Younan, M. et al. (2013). Microevolution of highly pathogenic avian influenza A(H5N1) viruses isolated from humans, Egypt, 2007-2011. Emerg Infect Dis 19:43-50.

---

What is claimed is:

1. An isolated modified H5 protein selected from the group consisting of a modified H5 protein having the amino acid sequence set forth in SEQ ID NO:6 and a modified H5 protein having the amino acid sequence set forth in SEQ ID NO:8.

2. The isolated modified H5 protein of claim 1, wherein the modified H5 protein has the amino acid sequence set forth in SEQ ID NO:6.

3. The isolated modified H5 protein of claim 1, wherein the modified H5 protein has the amino acid sequence set forth in SEQ ID NO:8.

4. A nucleic acid molecule encoding the modified H5 protein of claim 1.

5. The nucleic acid molecule of claim 4, wherein the nucleic acid molecule has the nucleotide sequence set forth in SEQ ID NO:5.

6. The nucleic acid molecule of claim 4, wherein the nucleic acid molecule has the nucleotide sequence set forth in SEQ ID NO:7.

7. A vector comprising the nucleic acid molecule of claim 4.

8. An isolated host cell comprising the vector of claim 7.

9. A recombinant avian influenza virus comprising the modified H5 protein of claim 1.

10. The recombinant avian influenza virus of claim 9, which comprises a nucleic acid molecule encoding the modified H5 protein.

11. The recombinant avian influenza virus of claim 10, wherein the nucleic acid molecule has the nucleotide sequence set forth in SEQ ID NO:5.

12. The recombinant avian influenza virus of claim 10, wherein the nucleic acid molecule has the nucleotide sequence set forth in SEQ ID NO:7.

13. A composition comprising the modified H5 protein of claim 1.

14. A composition comprising the recombinant avian influenza virus of claim 9.

15. The composition of claim 13, which further comprises a pharmaceutically acceptable carrier.

16. The composition of claim 13, which further comprises an adjuvant.

17. The composition of claim 13, which is a vaccine.

18. A method of eliciting a protective immune response to an avian influenza virus in a subject comprising administering a prophylactically effective amount of the composition of claim 13 to a subject.

19. A method of treating or preventing a disease associated with an avian influenza virus comprising administering the composition of claim 13 to a subject.

20. A method of the treatment or prophylaxis of avian influenza virus infections comprising administering a therapeutically effective amount of the composition of claim 13 to a subject in need of such a treatment.

21. A method of preventing a subject from becoming afflicted with an avian influenza-associated disease comprising administering to the subject a prophylactically, therapeutically or immunologically effective amount of the composition of claim 13.

22. A method of delaying the onset of or slowing the rate of an avian influenza-associated disease in an avian influenza-infected subject comprising
administering to the subject a prophylactically, therapeutically or immunologically effective amount of the composition of claim 13.

23. A vaccine comprising (i) one or more immunogenic agents selected from the group consisting of (a) the modified H5 protein of claim 1, (b) a nucleic acid molecule of encoding the modified H5 protein of (a), (c) a vector comprising the nucleic acid molecule of (b), (d) a recombinant avian influenza virus comprising the modified H5 protein of (a) and (e) combinations thereof and (ii) a pharmaceutically acceptable carrier and/or excipient.

24. The vaccine of claim 23, wherein the excipient is one or more adjuvants.

25. A method of eliciting a protective immune response to an avian influenza virus in a subject comprising administering a prophylactically effective amount of the vaccine of claim 22 to a subject.

26. A method of treating or preventing a disease associated with an avian influenza virus comprising administering the vaccine of claim 23 to a subject.

27. A method of the treatment or prophylaxis of avian influenza virus infections comprising administering a therapeutically effective amount of the composition of claim 23 a subject in need of such a treatment.

28. A method of preventing a subject from becoming afflicted with an avian influenza-associated disease comprising administering to the subject a prophylactically, therapeutically or immunologically effect amount of the vaccine of claim 23.

29. A method of delaying the onset of or slowing the rate of an avian influenza-associated disease in an avian influenza-infected subject comprising administering to the subject a prophylactically, therapeutically or immunologically effect amount of the vaccine of claim 23.

30. A kit for immunization of a subject to avian influenza comprising (i) one or more immunogenic agents selected from the group consisting of (a) the modified H5 protein of claim 1, (b) a nucleic acid molecule encoding the modified H5 protein of (a), (c) a vector comprising the nucleic acid molecule of (b), (d) a recombinant avian influenza virus comprising the modified H5 protein of (a), (e) a vaccine comprising (a), (b), (c) or (d) and (f) combinations thereof, and (ii) an instructional material for the use thereof.

31. The kit of claim 30, which further comprises an applicator.

32. A method of making a vaccine using one or more immunogenic agents selected from the group consisting of (a) the modified H5 protein of claim 1, (b) a nucleic acid molecule encoding the modified H5 protein molecule of (a), (c) a vector comprising the nucleic acid molecule of (b), (d) a recombinant avian influenza virus comprising the modified H5 protein of (a) and (e) combinations thereof.

* * * * *